(12) United States Patent
Bernis et al.

(10) Patent No.: US 7,592,340 B2
(45) Date of Patent: Sep. 22, 2009

(54) QUINOXALINES USEFUL AS INHIBITORS OF PROTEIN KINASES

(75) Inventors: Guy W. Bernis, Arlington, MA (US); John P. Duffy, Northborough, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 544 days.

(21) Appl. No.: 11/004,657

(22) Filed: Dec. 3, 2004

(65) Prior Publication Data
US 2005/0234064 A1  Oct. 20, 2005

Related U.S. Application Data

(60) Provisional application No. 60/526,843, filed on Dec. 4, 2003.

(51) Int. Cl.
| | |
|---|---|
| C07D 241/42 | (2006.01) |
| C07D 241/44 | (2006.01) |
| A61K 31/498 | (2006.01) |
| A61P 35/04 | (2006.01) |
| A61P 37/02 | (2006.01) |
| A61P 25/28 | (2006.01) |

(52) U.S. Cl. .................. 514/249; 544/353; 544/354; 544/355; 544/356

(58) Field of Classification Search ............... 514/249; 544/354, 355, 356, 353
See application file for complete search history.

(56) References Cited

U.S. PATENT DOCUMENTS

| 6,348,461 B1 * | 2/2002 | Takano et al. ............ 514/232.5 |
| 2002/0091124 A1 | 7/2002 | Beckers et al. |
| 2003/0158216 A1 | 8/2003 | Beckers et al. |
| 2003/0207886 A1 | 11/2003 | Plucker et al. |
| 2006/0183909 A1 | 8/2006 | Schmitt et al. |

FOREIGN PATENT DOCUMENTS

| WO | WO 92/11245 A1 | 7/1992 |
| WO | 9822460 A1 | 5/1998 |
| WO | 9964400 A1 | 12/1999 |
| WO | 0023448 A1 | 4/2000 |
| WO | 0042022 A1 | 7/2000 |
| WO | 0045800 A2 | 8/2000 |
| WO | WO 00/76980 A1 | 12/2000 |
| WO | 0174786 A1 | 10/2001 |
| WO | 0181340 A2 | 11/2001 |
| WO | 0204425 A2 | 1/2002 |
| WO | 02060874 A1 | 8/2002 |
| WO | WO 02/060482 A2 | 8/2002 |
| WO | 02074763 A1 | 9/2002 |
| WO | 03000690 A1 | 1/2003 |
| WO | 03006670 A2 | 1/2003 |
| WO | WO 03/000688 A1 | 1/2003 |
| WO | 03035065 A1 | 5/2003 |
| WO | 03053970 A1 | 7/2003 |
| WO | 03068756 A1 | 8/2003 |
| WO | 03101990 A1 | 12/2003 |
| WO | 2004006912 A2 | 1/2004 |
| WO | 2004006931 A2 | 1/2004 |
| WO | 2004009600 A1 | 1/2004 |
| WO | 2004024897 A2 | 3/2004 |
| WO | 2004043913 A2 | 5/2004 |

OTHER PUBLICATIONS

Hayashi et al, "Quinoxalines. XII. Reaction of 2-(methylsulfonyl)-quinoxaline with active methylene compounds" Yakugaku Zasshi, vol. 87(9), pp. 1103-1108 (1967), as abstracted by CAS Online (CAPLUS).*

Dahn et al., "Uber γ-Aryl-α, β-diketo-butyramide," Helvetica Chim. Acta, 43:1555-1560 (1960); Database Beilstein accession No. BRN: 533330.

Ueda et al., "Diazepinoquinoxalines and imidazolobenzopteridines", J. Heterocyclic Chem. 33:169-172 (1996).

Ueda et al, "Reaction of lumichrome or 2-thiolumichrome with alkylamines", J. Heterocyclic Chem. 28:1485-1490 (1991).

Wolfgang Pfleiderer, "Uber die Kondensation von Methylalloxan mit 0-Phenylendiamin," Chem. Ber. 89: 1148-1151 (1956); Database Beilstein accession No. BRN: 190222.

Hayashi et al, "Quinoxalines on the Reaction of 2-(Methylsulfonyl)quinoxaline with Active Methylene Compounds", Yakugaku Zasshi,, 87: 1103-1107 (1967); Database Beilstein accession No. BRN: 647790.

Hayashi et al, "Studies on Quinoxaline N-Oxides. III. On N-Oxidation of 2-Substituted and 2,3-Disubstituted Quinoxalines", Yakugaku Zasshi, 84: 163-177 (1964); Database Beilstein accession No. BRN: 524503.

* cited by examiner

*Primary Examiner*—Brenda L Coleman
*Assistant Examiner*—Susanna Moore
(74) *Attorney, Agent, or Firm*—Jennifer G. Che; Vertex Pharmaceuticals Incorporated

(57) ABSTRACT

The present invention relates to compounds of formula I useful as inhibitors of protein kinases. The invention also provides pharmaceutically acceptable compositions comprising said compounds and methods of using the compositions in the treatment of various disease, conditions, or disorders.

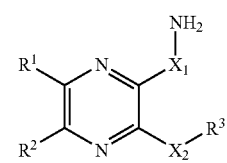

28 Claims, No Drawings

US 7,592,340 B2

QUINOXALINES USEFUL AS INHIBITORS OF PROTEIN KINASES

CROSS REFERENCE TO RELATED APPLICATIONS

This present application claims the benefit, under 35 U.S.C. §119, to U.S. Provisional Application No. 60/526,843 filed Dec. 4, 2003, the entire disclosure of which is incorporated herein by reference.

TECHNICAL FIELD OF THE INVENTION

The present invention relates to compounds useful as inhibitors of protein kinases. The invention also provides pharmaceutically acceptable compositions comprising the compounds of the invention and methods of using the compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S. *The Protein Kinase Facts Book, I and II*, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., *FASEB J.* 1995, 9, 576-596; Knighton et al., *Science* 1991, 253, 407-414; Hiles et al., *Cell* 1992, 70, 419-429; Kunz et al., *Cell* 1993, 73, 585-596; Garcia-Bustos et al., *EMBO J.* 1994, 13, 2352-2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there has been a substantial effort in medicinal chemistry to find protein kinase inhibitors that are effective as therapeutic agents.

Glycogen synthase kinase-3 (GSK-3) is a serine/threonine protein kinase comprised of α and β forms that are each encoded by distinct genes [Coghlan et al., *Chemistry & Biology* 2000, 7, 793-803; and Kim and Kimmel, *Curr. Opinion Genetics Dev.*, 2000 10, 508-514]. GSK-3 has been implicated in various diseases including diabetes, Alzheimer's disease, CNS disorders such as manic depressive disorder and neurodegenerative diseases, and cardiomyocyte hypertrophy [PCT Application Nos.: WO 99/65897 and WO 00/38675; and Haq et al., *J. Cell Biol.* 2000, 151, 117-130]. These diseases are associated with the abnormal operation of certain cell signaling pathways in which GSK-3 plays a role. GSK-3 has been found to phosphorylate and modulate the activity of a number of regulatory proteins. These proteins include glycogen synthase, which is the rate limiting enzyme necessary for glycogen synthesis, the microtubule associated protein Tau, the gene transcription factor β-catenin, the translation initiation factor e1F2B, as well as ATP citrate lyase, axin, heat shock factor-1, c-Jun, c-myc, c-myb, CREB, and CEPBα. These diverse protein targets implicate GSK-3 in many aspects of cellular metabolism, proliferation, differentiation, and development.

In a GSK-3 mediated pathway that is relevant for the treatment of type II diabetes, insulin-induced signaling leads to cellular glucose uptake and glycogen synthesis. Along this pathway, GSK-3 is a negative regulator of the insulin-induced signal. Normally, the presence of insulin causes inhibition of GSK-3 mediated phosphorylation and deactivation of glycogen synthase. The inhibition of GSK-3 leads to increased glycogen synthesis and glucose uptake [Klein et al., *PNAS* 1996, 93, 8455-8459; Cross et al., *Biochem. J.* 1994, 303, 21-26); Cohen, *Biochem. Soc. Trans.* 1993, 21, 555-567; and Massillon et al., *Biochem J.* 1994, 299, 123-128]. However, in a diabetic patient, where the insulin response is impaired, glycogen synthesis and glucose uptake fail to increase despite the presence of relatively high blood levels of insulin. This leads to abnormally high blood levels of glucose with acute and long-term effects that may ultimately result in cardiovascular disease, renal failure and blindness. In such patients, the normal insulin-induced inhibition of GSK-3 fails to occur. It has also been reported that in patients with type II diabetes, GSK-3 is overexpressed [see, PCT Application: WO 00/38675]. Therapeutic inhibitors of GSK-3 are therefore potentially useful for treating diabetic patients suffering from an impaired response to insulin.

GSK-3 activity is associated with Alzheimer's disease. This disease is characterized by the well-known β-amyloid peptide and the formation of intracellular neurofibrillary tangles.

Amyloid-β plaques, formed by the aggregation of these β-amyloid peptides, are one of the pathological hallmarks of Alzheimer's disease. It has been shown that GSK-3α inhibition reduces amyloid-β peptides in an animal model of Alzheimer's disease. See pages 435, 438. Phiel et. al., *Nature* 423, 435-439 (2003). Mice over-expressing amyloid precursor protein (APP) treated with lithium (a GSK-3α inhibitor) over a three-week period showed over a 50% decrease in amyloid-13 peptide tissue levels.

The neurofibrillary tangles contain hyperphosphorylated Tau protein, in which Tau is phosphorylated on abnormal sites. GSK-3 is known to phosphorylate these abnormal sites in cell and animal models. Furthermore, inhibition of GSK-3 has been shown to prevent hyperphosphorylation of Tau in cells [Lovestone et al., *Current Biology* 1994, 4, 1077-86; and Brownlees et al., *Neuroreport* 1997, 8, 3251-55]. Therefore, GSK-3 activity promotes generation of the neurofibrillary tangles and the progression of Alzheimer's disease.

Another substrate of GSK-3 is β-catenin, which is degradated after phosphorylation by GSK-3. Reduced levels of β-catenin have been reported in schizophrenic patients and have also been associated with other diseases related to increase in neuronal cell death [Zhong et al., *Nature* 1998, 395, 698-702; Takashima et al., *PNAS* 1993, 90, 7789-93; and Pei et al., *J. Neuropathol. Exp* 1997, 56, 70-78].

GSK-3 activity is associated with stroke [Wang et al., *Brain Res* 2000, 859, 381-5; Sasaki et al., *Neurol Res* 2001, 23, 588-92; Hashimoto et al., *J. Biol. Chem* 2002, 277, 32985-32991].

The Janus kinases (JAK) are a family of tyrosine kinases consisting of JAK1, JAK2, JAK3 and TYK2. The JAKs play a critical role in cytokine signaling. The down-stream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematologic malignancies such as leukemias and lymphomas. The pharmaceutical intervention in the JAK/STAT pathway has been reviewed [Frank *Mol. Med.* 1999, 5, 432-456 and Seidel et al., *Oncogene* 2000, 19, 2645-2656].

JAK1, JAK2, and TYK2 are ubiquitously expressed, while JAK3 is predominantly expressed in hematopojetic cells. JAK3 binds exclusively to the common cytokine receptor gamma chain ($\gamma_c$) and is activated by IL-2, IL-4, IL-7, IL-9, and IL-15. The proliferation and survival of murine mast cells induced by IL-4 and IL-9 have, in fact, been shown to be dependent on JAK3- and $\gamma_c$-signaling [Suzuki et al., *Blood* 2000, 96, 2172-2180].

Cross-linking of the high-affinity immunoglobulin (Ig) E receptors of sensitized mast cells leads to a release of proinflammatory mediators, including a number of vasoactive cytokines resulting in acute allergic, or immediate (type I) hypersensitivity reactions [Gordon et al., *Nature* 1990, 346, 274-276 and Galli, *N. Engl. J. Med.* 1993, 328, 257-265]. A crucial role for JAK3 in IgE receptor-mediated mast cell responses in vitro and in vivo has been established [Malaviya et al., *Biochem. Biophys. Res. Commun.* 1999, 257, 807-813]. In addition, the prevention of type I hypersensitivity reactions, including anaphylaxis, mediated by mast cell-activation through inhibition of JAK3 has also been reported [Malaviya et al., *J. Biol. Chem.* 1999 274, 27028-27038]. Targeting mast cells with JAK3 inhibitors modulated mast cell degranulation in vitro and prevented IgE receptor/antigen-mediated anaphylactic reactions in vivo.

A recent study described the successful targeting of JAK3 for immunosuppression and allograft acceptance. The study demonstrated a dose-dependent survival of Buffalo heart allograft in Wistar Furth recipients upon administration of inhibitors of JAK3 indicating the possibility of regulating unwanted immune responses in graft versus host disease [Kirken, *Transpl. Proc.* 2001, 33, 3268-3270].

IL-4-mediated STAT-phosphorylation has been implicated as the mechanism involved in early and late stages of rheumatoid arthritis (RA). Up-regulation of proinflammatory cytokines in RA synovium and synovial fluid is a characteristic of the disease. It has been demostrated that IL-4-mediated activation of IL-4/STAT pathway is mediated through the Janus Kinases (JAK 1 & 3) and that IL-4-associated JAK kinases are expressed in the RA synovium [Muller-Ladner et al., *J. Immunol.* 2000, 164, 3894-3901].

Familial amyotrophic lateral sclerosis (FALS) is a fatal neurodegenerative disorder affecting about 10% of ALS patients. The survival rates of FALS mice were increased upon treatment with a JAK3 specific inhibitor. This suggested that JAK3 plays a role in FALS [Trieu et al., *Biochem. Biophys. Res. Commun.* 2000, 267, 22-25].

Signal transducer and activator of transcription (STAT) proteins are activated by, among others, the JAK family kinases. Results from a recent study suggested the possibility of intervention in the JAK/STAT signaling pathway by targeting JAK family kinases with specific inhibitors for the treatment of leukemia [Sudbeck et al., *Clin. Cancer Res.* 1999, 5, 1569-1582]. JAK3 specific compounds were shown to inhibit the clonogenic growth of JAK3-expressing cell lines DAUDI, RAMOS, LC1-19, NALM-6, MOLT-3 and HL-60.

In animal models, TEL/JAK2 fusion proteins have induced myeloproliferative disorders and in hematopoietic cell lines, and introduction of TEL/JAK2 resulted in activation of STAT1, STAT3, STAT5, and cytokine-independent growth [Schwaller et al., *EMBO J.* 1998, 17, 5321-5333].

Inhibition of JAK3 and TYK2 abrogated tyrosine phosphorylation of STAT3, and inhibited cell growth of mycosis fungoides, a form of cutaneous T-cell lymphoma. These results implicated JAK family kinases in the constitutively activated JAK/STAT pathway that is present in mycosis fungoides [Nielsen et al., *Proc. Nat. Acad. Sci. U.S.A.* 1997, 94, 6764-6769]. Similarly, STAT3, STAT5, JAK1 and JAK2 were demonstrated to be constitutively activated in mouse T-cell lymphoma characterized initially by LCK over-expression, thus further implicating the JAK/STAT pathway in abnormal cell growth [Yu et al., *J. Immunol.* 1997, 159, 5206-5210]. In addition, IL-6-mediated STAT3 activation was blocked by an inhibitor of JAK, leading to sensitization of myeloma cells to apoptosis [Catlett-Falcone et al., *Immunity* 1999, 10, 105-115].

Syk is a tyrosine kinase that plays a critical role in FcɛRI mediated mast cell degranulation and eosinophil activation. Accordingly, Syk kinase is implicated in various allergic disorders, in particular asthma. It has been shown that Syk binds to the phosphorylated gamma chain of the FcɛRI receptor via N-terminal SH2 domains and is essential for down-stream signaling [Taylor et al., *Mol. Cell. Biol.* 1995, 15, 4149].

Inhibition of eosinophil apoptosis has been proposed as a key mechanism for the development of blood and tissue eosinophilia in asthma. IL-5 and GM-CSF are upregulated in asthma and are proposed to cause blood and tissue eosinophilia by inhibition of eosinophil apoptosis. Inhibition of eosinophil apoptosis has been proposed as a key mechanism for the development of blood and tissue eosinophilia in asthma. It has been reported that Syk kinase is required for the prevention of eosinophil apoptosis by cytokines (using antisense)[Yousefi et al., *J. Exp. Med.* 1996, 183, 1407].

The role of Syk in FcγR dependent and independent response in bone marrow derived macrophages has been determined by using irradiated mouse chimeras reconstituted with fetal liver cells from Syk −/− embryos. Syk deficient macrophages were defective in phagocytosis induced by FcγR but showed normal phagocytosis in response to complement [Kiefer et al., *Mol. Cell. Biol.* 1998, 18, 4209]. It has also been reported that aerosolized Syk antisense suppresses Syk expression and mediator release from macrophages [Stenton et al., *J. Immunology* 2000, 164, 3790].

Accordingly, there is a great need to develop compounds useful as inhibitors of protein kinases. In particular, it would be desirable to develop compounds that are useful as inhibitors of SYK, JAK-3, or GSK-3, particularly given the inadequate treatments currently available for the majority of the disorders implicated in their activation.

SUMMARY OF THE INVENTION

It has now been found that compounds of this invention, and pharmaceutically acceptable compositions thereof, are effective as inhibitors of protein kinases. In certain embodiments, these compounds are effective as inhibitors of SYK, JAK-3, or GSK-3, protein kinases. These compounds have the general formula I:

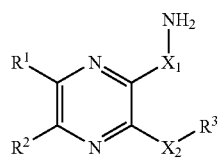

I or a pharmaceutically acceptable salt thereof, wherein $R^1$, $R^2$, $R^3$, $X_1$, and $X_2$ are as defined below.

These compounds and pharmaceutically acceptable compositions thereof are useful for treating or preventing a variety of diseases, disorders or conditions, including, but not limited to, immunodeficiency disorders, inflammatory diseases, allergic diseases, autoimmune diseases, proliferative disorders, immunologically-mediated diseases, or respiratory disorders, to name a few. The compounds provided by this invention are also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

I. General Description of Compounds of the Invention

The present invention relates to a compound of formula I:

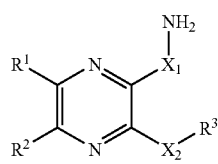

I or a pharmaceutically acceptable salt thereof, wherein:
$R^1$ and $R^2$ are each independently halogen or -L-R'; or $R^1$ and $R^2$, taken together, form an optionally substituted 5- or 6-membered monocyclic aryl ring having 0-5 heteroatoms independently selected from nitrogen, oxygen, or sulfur; or a 5-, 6-, or 7-membered saturated or partially unsaturated monocyclic ring having 0-3 heteroatoms independently selected from nitrogen, oxygen, or sulfur, wherein any ring formed by $R^1$ and $R^2$ taken together is optionally substituted at one or more substituable carbon or nitrogen atoms with n independent occurrences of Q-$R^X$, wherein n is 0-5;

L is a bond or is an optionally substituted $C_{1-6}$ alkylidene chain wherein up to two non-adjacent methylene units of L are optionally and independently replaced by —CO—, —CO$_2$—, —COCO—, —CONR—, —OCONR—, —NRNR—, —NRNRCO—, —NRCO—, —NRCO$_2$—, —NRCONR—, —SO—, —SO$_2$—, —NRSO$_2$—, —SO$_2$NR—, —NRSO$_2$NR—, —O—, —S—, or —NR—;

each occurrence of R is independently selected from hydrogen or an optionally substituted $C_{1-6}$ aliphatic group; and each occurrence of R' is independently hydrogen or an optionally substituted group selected from $C_{1-8}$ aliphatic; a 5-6 membered monocyclic or an 8-10 membered bicyclic aryl group having 0-5 heteroatoms independently selected from nitrogen, oxygen, or sulfur; a 3-7-membered saturated or partially unsaturated monocyclic ring having 0-3 heteroatoms independently selected from nitrogen, oxygen, or sulfur; or an 8-10-membered saturated or partially unsaturated bicyclic ring system having 0-5 heteroatoms independently selected from nitrogen, oxygen, or sulfur, or wherein R and R' taken together, or two occurrences of R' taken together, form a 3-8 membered cycloalkyl, heterocyclyl, aryl, or heteroaryl ring having 0-3 heteroatoms independently selected from nitrogen, oxygen, or sulfur;

each independent occurrence of Q is a bond or is a $C_1$-$C_6$ alkylidene chain wherein up to two methylene units of Q are optionally replaced by —C(O)—, —C(S)—, —C(O)C(O)—, —CONR—, —CONRNR—, —CO$_2$—, —OC(O)—, —NRCO$_2$—, —O—, —NRCONR—, —OC(O)NR—, —NRNR, —NRCO—, —S—, —SO—, —SO$_2$—, —NR—, —SO$_2$NR—, or —NRSO$_2$—; and each occurrence of Rx is independently R', halogen, NO$_2$, or CN;

$X_1$ is C=O, S=O, SO$_2$, or C=NR;
$X_2$ is NR, S, O, or C(R)$_2$; and
$R^3$ is an optionally substituted group selected from: $C_{1-6}$ aliphatic; a 5-6 membered monocyclic or an 8-10 membered bicyclic aryl group having 0-5 heteroatoms independently selected from nitrogen, oxygen, or sulfur; a 3-8-membered saturated or partially unsaturated monocyclic ring having 0-3 heteroatoms independently selected from nitrogen, oxygen, or sulfur; or an 8-10-membered saturated or partially unsaturated bicyclic ring system having 0-5 heteroatoms independently selected from nitrogen, oxygen, or sulfur, wherein $R^3$ is optionally substituted with m independent occurrences of Z-$R^Y$, wherein m is 0-5; each independent occurrence of Z is a bond or is a $C_1$-$C_6$ alkylidene chain, wherein up to two methylene units of Z are optionally replaced by —C(O)—, —C(O)C(O)—, —CONR—, —CONRNR—, —CO$_2$—, —OC(O)—, —NRCO$_2$—, —O—, —NRCONR—, —OC(O)NR—, —NRNR, —NRCO—, —S—, —SO—, —SO$_2$—, —NR—, —SO$_2$NR—, or —NRSO$_2$—; and each occurrence of $R_Y$ is independently R', halogen, NO$_2$, or CN.

In certain embodiments, for compounds described directly above:
a) when $X_1$ is CO, then $R^2$ is not C(S)NH$_2$ or CN;
b) when $X_1$ is CO, $X_2$ is NH, and $R^2$ is 3,4-OMe-phenyl, then $R^3$ is not n-butyl;
c) when $X_1$ is CO and $X_2$ is CH$_2$, then $R^1$ and $R^2$ are not both hydrogen;
d) when $X_1$ is SO$_2$ and $X_2$ is O, then $R^1$ and $R^2$ are not both hydrogen;
e) when $R^1$ and $R^2$ are both hydrogen, $X_1$ is CO, and $X_2$ is SO$_2$ or NH, then $R^3$ is not unsubstituted benzyl, phenyl, or cyclohexyl;
f) when $R^1$ and $R^2$ are each methyl, then:
i) when $X_1$ is CO and $X_2$ is NH, then $R^3$ is not unsubstituted cyclohexyl or unsubstituted benzyl; and ii) when $X_1$ is CO and $X_2$ is $CH_2$, then $R^3$ is not unsubstituted benzyl;

g) when $R^1$ and $R^2$, taken together, are unsubstituted phenyl, then:
   i) when $X_1$ is CO and $X_2$ is $CH_2$, then $R^3$ is not substituted furyl, 2-Cl-phenyl, 3,5-dimethyl-2-benzofuranyl, 3,7-dimethyl-2-benzofuranyl, or 4-OMe-phenyl;
   ii) when $X_1$ is CO and $X_2$ is NH, then $R^3$ is not 2,4-dichloro-phenyl, 4-Cl-phenyl, 4-Me-phenyl, or unsubstituted phenyl, cyclohexyl, or benzyl; and
   iii) when $X_1$ is CO and $X_2$ is CHOH, then $R^1$ is not unsubstituted phenyl or —CHOHCH$_2$OH;

h) when $R^1$ and $R^2$, taken together, are unsubstituted cyclohexyl, then:
   i) when $X_1$ is CO and $X_2$ is $CH_2$, then $R^3$ is not unsubstituted phenyl; and
   ii) when $X_1$ is CO and $X_2$ is NH, then $R_3$ is not unsubstituted benzyl or cyclohexyl; and i) when $R^1$ and $R^2$, taken together, are 6,7-Me-phenyl, $X_1$ is CO, and $X_2$ is NH, then $R^3$ is not n-hexyl, n-butyl, n-propyl, or —CH$_2$CH=CH$_2$ In other embodiments, for compounds described directly above:

a) when $X_1$ is CO, then $R^1$ is not C(S)NH$_2$ or CN;
b) when $X_1$ is CO, $X_2$ is NH, and $R^2$ is 3,4-OMe-phenyl, then $R^3$ is not n-butyl;
c) when $X_1$ is CO and $X_2$ is $CH_2$, then $R^1$ and $R^2$ are not both hydrogen;
d) when $X_1$ is SO$_2$ and $X_2$ is O, then $R^1$ and $R^2$ are not both hydrogen;
e) when $R^1$ and $R^2$ are both hydrogen, $X_1$ is CO, and $X_2$ is SO$_2$ or NH, then $R^3$ is not unsubstituted benzyl, phenyl, or cyclohexyl;
f) when $R^1$ and $R^2$ are each methyl, then:
   i) when $X_1$ is CO and $X_2$ is NH, then $R^3$ is not unsubstituted cyclohexyl or unsubstituted benzyl; and
   ii) when $X_1$ is CO and $X_2$ is $CH_2$, then $R^3$ is not unsubstituted benzyl;
g) when $R^1$ and $R^2$, taken together, are unsubstituted phenyl, then:
   i) when $X_1$ is CO and $X_2$ is CH, then $R^3$ is not unsubstituted phenyl or OH;
   ii) when $X_1$ is CO and $X_2$ is $CH_2$, then $R^3$ is not methyl, unsubstituted phenyl, substituted furyl, 2-Cl-phenyl, 3,5-dimethyl-2-benzofuranyl, 3,7-dimethyl-2-benzofuranyl, or 4-OMe-phenyl;
   iii) when $X_1$ is CO and $X_2$ is NH, then $R^3$ is not methyl, —C(O)CH$_3$, C(O)O(C$_{1-3}$alkyl), C(O)C(O)OH, C(O)C(O)O(C$_{1-3}$alkyl), unsubstituted phenyl, cyclohexyl, benzyl, substituted benzofuranyl, 2,4-dichloro-phenyl, 4-Cl-phenyl, or 4-Me-phenyl;
   iv) when $X_1$ is CO and $X_2$ is NMe, then $R^3$ is not methyl;
   v) when $X_1$ is CO and $X_2$ is O, then $R^3$ is not methyl;
   vi) when $X_1$ is CO and $X_2$ is CHOH, then $R^1$ is not unsubstituted phenyl or —CHOHCH$_2$OH;

h) when $R^1$ and $R^2$, taken together, are unsubstituted cyclohexyl, then:
   i) when $X_1$ is CO and $X_2$ is $CH_2$, then $R^3$ is not unsubstituted phenyl;
   ii) when $X_1$ is CO and $X_2$ is NH, then $R_3$ is not unsubstituted benzyl or cyclohexyl; and i) when $X_1$ is CO and $X_2$ is NH, then:
   i) when $R^1$ and $R^2$, taken together, are 6,7-Me-phenyl, then $R^3$ is not n-hexyl, n-butyl, n-propyl, —CH$_2$CH=CH$_2$, —CH=N—CH$_2$CH=CH$_2$, C(=O)NR, C(=O)OR wherein R is H or C$_{1-3}$ alkyl;
   ii) when $R^1$ and $R^2$, taken together, are 6-NHAc-7-Me-phenyl, then $R^3$ is not —C(=O)CH$_3$;
   iii) when $R^1$ and $R^2$, taken together, are 6,7-OMe-phenyl, then $R^3$ is not C(O)C(O)OH or C(O)C(O)O(C$_{1-3}$alkyl);
   iv) when $R^1$ and $R^2$, taken together, are substituted pyrimidine, then $R^3$ is not —C(=O)CH$_3$;

j) when $X_1$ is CO and $X_2$ is O, then:
   i) when $R^1$ and $R^2$, taken together, are 6,7-Cl-phenyl, then $R^3$ is not methyl or —CH$_2$CH=CH$_2$;
   ii) when $R^1$ and $R^2$, taken together, are 6-NO$_2$-7-F-phenyl, then $R^3$ is not methyl.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$(as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halogen; —R$^o$; —OR$^o$; —SR$^o$; 1,2-methylenedioxy; 1,2-ethylenedioxy; phenyl (Ph) optionally substituted with R$^o$; —O(Ph) optionally substituted with R$^o$; —(CH$_2$)$_{1-2}$(Ph), optionally substituted with R$^o$; —CH=CH(Ph), optionally substituted with R$^o$; —NO$_2$; —CN; —N(R$^o$)$_2$; —NR$^o$C(O)R$^o$; —NR$^o$C(S) R$^o$; —NR$^o$C(O)N(R$^o$)$_2$; —NR$^o$C(S)N(R$^o$)$_2$; —NR$^o$CO$_2$R$^o$; —NR$^o$ NR$^o$C(O)R$^o$; —NR$^o$NR$^o$C(O)N(R$^o$)$_2$; —NR$^o$NR$^o$CO$_2$R$^o$; —C(O)C(O)R$^o$; —C(O)CH$_2$C(O)R$^o$; —CO$_2$R$^o$; —C(O)R$^o$; —C(S)R$^o$; —C(O)N(R$^o$)$_2$; —C(S)N (R$^o$)$_2$; —OC(O)N(R$^o$)$_2$; —OC(O)R$^o$; —C(O)N(OR$^o$)R$^o$; —C(NOR$^o$)R$^o$; —S(O)$_2$R$^o$; —S(O)$_3$R$^o$; —SO$_2$N(R$^o$)$_2$; —S(O)R$^o$; —NR$^o$SO$_2$N(R$^o$)$_2$; —NR$^o$SO$_2$R$^o$; —N(OR$^o$)R$^o$; —C(=NH)—N(R$^o$)$_2$; or —(CH$_2$)$_{0-2}$NHC(O)R$^o$ wherein each independent occurrence of R$^o$ is selected from hydrogen, optionally substituted C$_{1-6}$ aliphatic, an unsubstituted 5-6 membered heteroaryl or heterocyclic ring, phenyl, —O(Ph), or —CH$_2$(Ph), or, notwithstanding the definition above, two independent occurrences of R$^o$, on the same substituent or different substituents, taken together with the atom(s) to which each R$^o$ group is bound, form a 5-8-membered heterocyclyl, aryl, or heteroaryl ring or a 3-8-membered cycloalkyl ring having 0-3 heteroatoms independently selected from nitrogen, oxygen, or sulfur. Optional substituents on the aliphatic group of R$^o$ are selected from NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or haloC$_{1-4}$aliphatic, wherein each of the foregoing C$_{1-4}$aliphatic groups of R$^o$ is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O) R*, =NNHCO$_2$(alkyl), =NNHSO$_2$(alkyl), or =NR*, where each R* is independently selected from hydrogen or an optionally substituted C$_{1-6}$ aliphatic. Optional substituents on the aliphatic group of R* are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$aliphatic groups of R* is unsubstituted.

Optional substituents on the nitrogen of a non-aromatic heterocyclic ring are selected from —R$^+$, —N(R$^+$)$_2$, —C(O) R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N (R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$ (Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R$^+$, on the same substituent or different substituents, taken together with the atom(s) to which each R$^+$ group is bound, form a 5-8-membered heterocyclyl, aryl, or heteroaryl ring or a 3-8-membered cycloalkyl ring having 0-3 heteroatoms independently selected from nitrogen, oxygen, or sulfur. Optional substituents on the aliphatic group or the phenyl ring of R$^+$ are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo($C_{1-4}$ aliphatic), wherein each of the foregoing $C_{1-4}$aliphatic groups of $R^+$ is unsubstituted.

As described herein, a bond drawn from a substituent to the center of one ring within a multiple-ring system (as shown below), represents substitution of the substituent at any substitutable position in any of the rings within the multiple ring system. For example, Figure a represents possible substitution in any of the positions shown in Figure b.

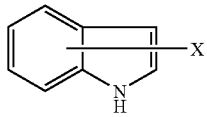

Figure a

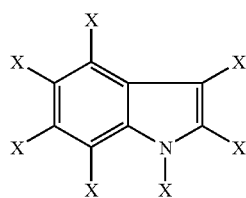

Figure b

The term "alkylidene chain" refers to a straight or branched carbon chain that may be fully saturated or have one or more units of unsaturation and has two points of attachment to the rest of the molecule.

As detailed above, in some embodiments, two independent occurrences of $R^o$ (or $R^+$, or any other variable similarly defined herein), are taken together together with the atom(s) to which each variable is bound to form a 5-8-membered heterocyclyl, aryl, or heteroaryl ring or a 3-8-membered cycloalkyl ring having 0-3 heteroatoms independently selected from nitrogen, oxygen, or sulfur. Exemplary rings that are formed when two independent occurrences of $R^o$ (or $R^+$, or any other variable similarly defined herein) are taken together with the atom(s) to which each variable is bound include, but are not limited to the following: a) two independent occurrences of $R^o$ (or $R^+$, or any other variable similarly defined herein) that are bound to the same atom and are taken together with that atom to form a ring, for example, N(RO)$_2$, where both occurrences of $R^o$ are taken together with the nitrogen atom to form a piperidin-1-yl, piperazin-1-yl, or morpholin-4-yl group; and b) two independent occurrences of $R^o$ (or $R^+$, or any other variable similarly defined herein) that are bound to different atoms and are taken together with both of those atoms to form a ring, for example where a phenyl group is substituted with two occurrences of $OR^o$

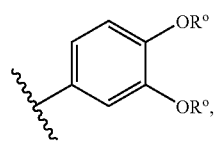

these two occurrences of $R^o$ are taken together with the oxygen atoms to which they are bound to form a fused 6-membered oxygen containing ring:

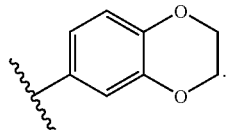

It will be appreciated that a variety of other rings can be formed when two independent occurrences of $R^o$ (or $R^+$, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

3. Description of Exemplary Compounds

As described generally above, $R^1$ and $R^2$ are each independently halogen or -L-$R^o$, or $R^1$ and $R^2$, taken together, form an optionally substituted 5- or 6-membered monocyclic aryl ring having 0-3 heteroatoms independently selected from nitrogen, oxygen, or sulfur or a 5-, 6-, or 7-membered saturated or partially unsaturated monocyclic ring having 0-5 heteroatoms independently selected from nitrogen, oxygen, or sulfur.

In certain embodiments, $R^1$ and $R^2$ are each independently halogen or -L-$R^o$. In other embodiments, $R^1$ and $R^2$ are each independently hydrogen, halogen, or an optionally substituted group selected from $C_{1-6}$alkyl, aryl, aryl($C_{1-6}$)alkyl, —N($R^o$)$_2$, —CH$_2$N($R^o$)$_2$, —OR', —CH$_2$OR', —SR', —CH$_2$SR', —COOR', —NRCOR', —(CH$_2$)$_2$N($R^o$)$_2$, —(CH$_2$)$_2$OR', —(CH$_2$)$_2$SR', —COR', —CON($R^o$)$_2$, —SO$_2$$R^o$, or —SO$_2$N($R^o$)$_2$. In yet other embodiments, $R^1$ and $R^2$ are each independently H, Cl, Br, F, CF$_3$, Me, Et, —COOH, NH$_2$, —N(CH$_3$)$_2$, —N(Et)$_2$, —N(iPr)$_2$, —O(CH$_2$)$_2$ OCH$_3$, —CO(C$_1$-C$_4$alkyl), —CONH$_2$, —COOCH$_3$, —OH, —CH$_2$OH, —NHCOCH$_3$, —SO$_2$(C$_1$-C$_4$alkyl), —SO$_2$NH$_2$, —SO$_2$N(CH$_3$)$_2$, or an optionally substituted group selected from $C_{1-4}$alkoxy, phenyl, phenyloxy, benzyl, or benzyloxy.

In other embodiments, $R^1$ and $R^2$, taken together, form an optionally substituted 5- or 6-membered monocyclic aryl ring having 0-5 heteroatoms independently selected from nitrogen, oxygen, or sulfur, or a 5-, 6-, 7-, or 8-membered saturated or partially unsaturated monocyclic ring having 0-3 heteroatoms independently selected from nitrogen, oxygen, or sulfur.

In certain embodiments, $R^1$ and $R^2$, taken together, form an optionally substituted 5- or 6-membered monocyclic aryl ring having 0-5 heteroatoms independently selected from nitrogen, oxygen, or sulfur.

In other embodiments, $R^1$ and $R^2$, taken together, form an optionally substituted 5-, 6-, 7-, or 8-membered saturated or partially unsaturated monocyclic ring having 0-3 heteroatoms independently selected from nitrogen, oxygen, or sulfur.

In another embodiment, $R^1$ and $R^2$, taken together, form an optionally substituted 6-membered monocyclic aryl ring having 0-5 heteroatoms independently selected from nitrogen, oxygen, or sulfur.

In preferred embodiments, $R^1$ and $R^2$ are taken together to form a ring and compounds have one of the structures depicted below:

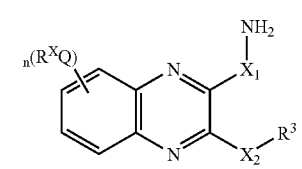
I-A

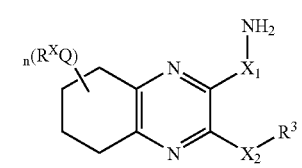
I-B

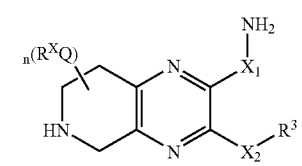
I-C

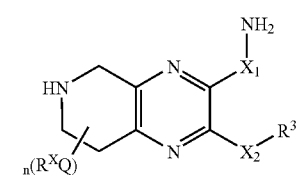
I-D

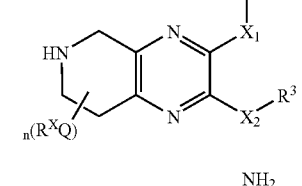
I-E

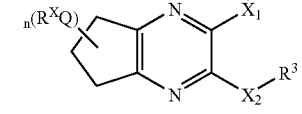
I-F

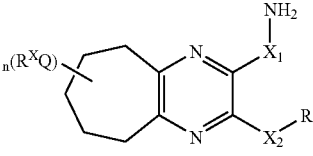
I-G

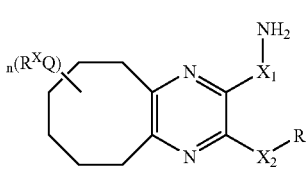

-continued

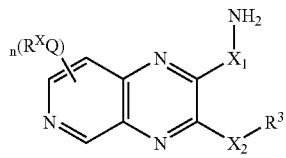
I-H

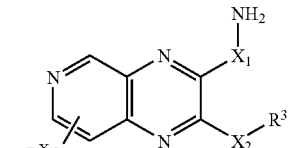
I-I

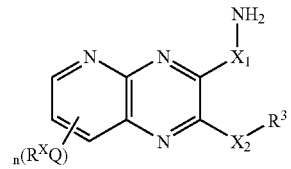
I-J

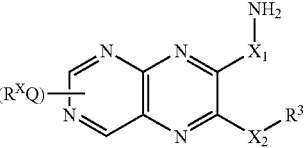
I-K

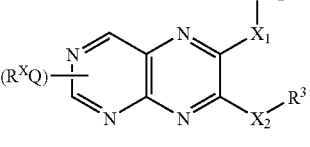
I-L

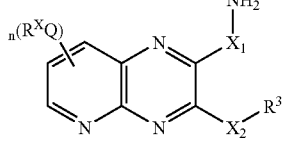
I-M

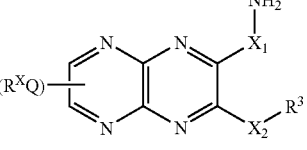
I-N

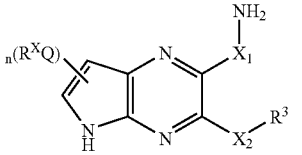
I-O

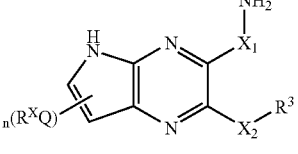
I-P

-continued

I-Q 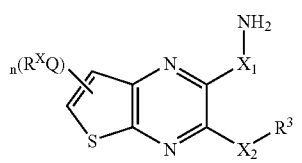

I-R 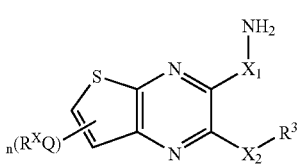

I-S 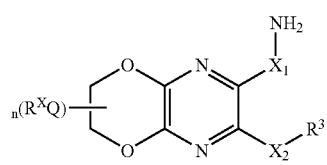

I-T 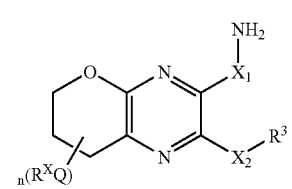

I-U 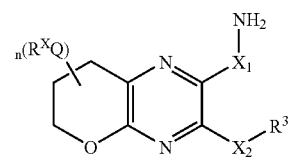

I-V 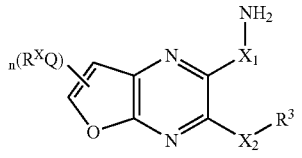

I-W 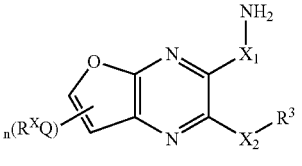

I-X 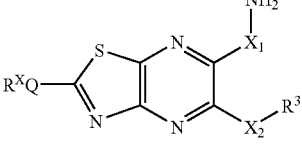

I-Y 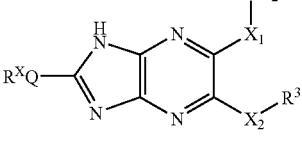

-continued

I-Z 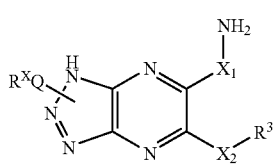

I-AA 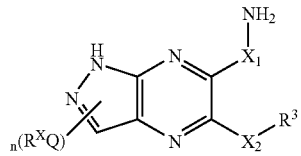

I-BB 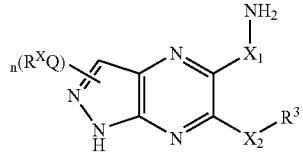

I-CC 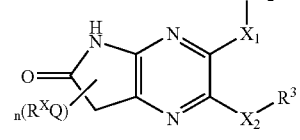

I-DD 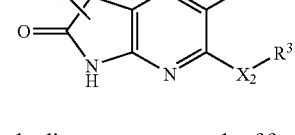

In other embodiments, compounds of formula I-A, I-H, I-I, I-J, I-K, I-L, I-M, or I-N are provided.

In other embodiments, compounds of formula I-A are provided.

It will also be appreciated that one or more hydrogen atoms on any substitutable nitrogen or carbon atom may optionally be substituted with n independent occurrences of Q-R$^X$, wherein n is 0-5.

In certain embodiments, each occurrence of Q is a bond or $C_1$-$C_6$ alkylidene chain, wherein up to two methylene units of Q are optionally replaced by —C(O)—, —C(O)C(O)—, —CONR—, —CONRNR—, —CO$_2$—, —OC(O)—, —NRCO$_2$—, —O—, —NRCONR—, —OC(O)NR—, —NRNR—, —NRCO—, —S—, —SO—, —SO$_2$—, —NR—, —SO$_2$NR—, or —NRSO$_2$—. In other embodiments, each occurrence of Q is optionally substituted $C_1$-$C_6$alkyl wherein up to two methylene units of the alkyl chain are optionally replaced by —C(O)—, —CONR—, —CO$_2$—, —OC(O)—, —NRCO$_2$—, —O—, —NRCONR—, —NRCO—, —S—, —SO—, —SO$_2$—, or —NR—.

In some embodiments, each R$^X$ is independently R$^o$. In other embodiments, each R$^X$ is H. In other embodiments, each R$^X$ is independently halogen, NO$_2$, or CN.

In certain preferred embodiments, n is 0-4, and each occurrence of Q-R$^X$, when present, is independently halogen, CN, NO$_2$, or an optionally substituted group selected from $C_{1-4}$alkyl, aryl, aralkyl, heteroaryl, a cycloalkyl or heterocloalkyl group having 3-10 atoms, —N(R')$_2$, —CH$_2$N(R')$_2$, —OR', —CH$_2$OR', —SR', —CH$_2$SR', —COOR', —NRCOR', —CON(R')$_2$, or —S(O)$_2$N(R')$_2$.

In other preferred embodiments, each occurrence of Q-R$^X$, when present, is Cl, Br, F, CF$_3$, methyl, ethyl, propyl, butyl, CN, —COOH, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —OCH$_2$CH$_2$CH$_3$, —OCH$_2$CH$_2$CH$_2$CH$_3$, —CH$_2$OH, —NHCOCH$_3$, —SO$_2$NH$_2$, —NHCO(pyridyl), —NHCONH$_2$, —NH$_2$, —NHCO(CH$_2$)N(CH$_2$)$_2$, —NHCO(CH$_2$)NH$_2$, or an optionally substituted group selected from piperidinyl, piperizinyl, morpholino, phenyl, phenyloxy, benzyl, benzyloxy, pyridyl, pyrimidinyl, pyridazinyl, thiophene, furan, thiazole, oxazole, thiadiazole, oxadiazole, pyrazole, or pyrrole.

In some embodiments, each occurrence of Q-R$^X$, when present, is Cl, Br, F, CF$_3$, methyl, ethyl, propyl, butyl, CN, —COOH, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —OCH$_2$CH$_2$CH$_3$, —OCH$_2$CH$_2$CH$_2$CH$_3$, —CH$_2$OH, —NHCOCH$_3$, —SO$_2$NH$_2$, —NHCO(pyridyl), —NHCONH$_2$, —NH$_2$, —NHCO(CH$_2$)N(CH$_2$)$_2$, or —NHCO(CH$_2$)NH$_2$.

In other embodiments, each occurrence of Q-R$^X$, when present, is an optionally substituted group selected from piperidinyl, piperizinyl, morpholino, phenyl, phenyloxy, benzyl, benzyloxy, pyridyl, pyrimidinyl, pyridazinyl, thiophene, furan, thiazole, oxazole, thiadiazole, oxadiazole, pyrazole, or pyrrole.

In some embodiments each occurrence of QR$^X$, when present, is optionally substituted aryl. In other embodiments, each occurrence of Q-R$^X$, when present, is optionally substituted heteroaryl.

In other preferred embodiments, n is 2. In still other preferred embodiments, n is 1. In yet other preferred embodiments, n is 0.

In certain embodiments, any substitutable nitrogen atom on a ring formed by R$^1$ and R$^2$ taken together is substituted with hydrogen, or with an optionally substituted group selected from C$_1$-C$_6$alkyl, aryl, aryl(C$_1$-C$_6$)alkyl, —N(R')$_2$, —CH$_2$N(R')$_2$, —CH$_2$OR', —CH$_2$SR', —(CH$_2$)$_2$N(R')$_2$, —(CH$_2$)$_2$OR', —(CH$_2$)$_2$SR', —COR', —CON(R°)$_2$, SO$_2$R', or —S(O)$_2$N(R')$_2$. In more preferred embodiments, any substitutable nitrogen atom on a ring formed by R$^1$ and R$^2$, taken together is substituted with H, Me, CF$_3$, ethyl, propyl, butyl, pentyl, CO(C$_1$-C$_4$alkyl), —CONH$_2$, —COO(C$_1$-C$_4$alkyl), —CH$_2$OH, —SO$_2$(C$_1$-C$_4$alkyl), —SO$_2$NH$_2$, SO$_2$N(CH$_3$)$_2$, or optionally substituted phenyl or benzyl.

As described generally above, X$_1$ is C=O, S=O, SO$_2$, or C=NR. In preferred embodiments, X$^1$ is C=O or SO$_2$. In more preferred embodiments, X$^1$ is C=O and compounds have the structure:

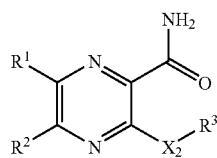

II wherein R$^1$, R$^2$, X$^2$ and R$^3$ are defined generally above, or in any of the classes and subclasses described above and herein.

As described generally above, X$_2$ is NR, S, O, or C(R°)$_2$. In some embodiments, X$_2$ is NR or C(R)$_2$. In other embodiments, X$_2$ is NR, O, or S. In yet other embodiments, X$_2$ is NR and compounds have the structure:

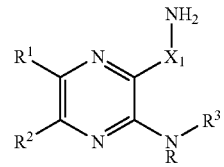

III

In another embodiments, X$_1$ is C=O and X$_2$ is NR and compounds have the structure:

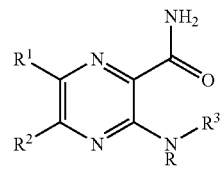

IV

As described generally above, R$^3$ is an optionally substituted group selected from: C$_{1-6}$ aliphatic; a 5-6 membered monocyclic or an 8-10 membered bicyclic aryl group having 0-5 heteroatoms independently selected from nitrogen, oxygen, or sulfur; a 3-8-membered saturated or partially unsaturated monocyclic ring having 0-3 heteroatoms independently selected from nitrogen, oxygen, or sulfur; or an 8-10-membered saturated or partially unsaturated bicyclic ring system having 0-5 heteroatoms independently selected from nitrogen, oxygen, or sulfur, wherein R$^3$ is optionally substituted with m independent occurrences of Z-R$^Y$, wherein m is 0-5.

In certain preferred embodiments, R$^3$ is a 5-6 membered monocyclic or an 8-10 membered bicyclic aryl group having 0-5 heteroatoms independently selected from nitrogen, oxygen, or sulfur; a 3-8-membered saturated or partially unsaturated monocyclic ring having 0-3 heteroatoms independently selected from nitrogen, oxygen, or sulfur; or an 8-10-membered saturated or partially unsaturated bicyclic ring system having 0-5 heteroatoms independently selected from nitrogen, oxygen, or sulfur.

In other preferred embodiments, R$^3$ is an optionally substituted C$_{1-6}$aliphatic group, wherein the C$_{1-6}$aliphatic group is optionally substituted with a 5-6 membered monocyclic or an 8-10 membered bicyclic aryl group having 0-5 heteroatoms independently selected from nitrogen, oxygen, or sulfur; a 3-8-membered saturated or partially unsaturated monocyclic ring having 0-3 heteroatoms independently selected from nitrogen, oxygen, or sulfur; or an 8-10-membered saturated or partially unsaturated bicyclic ring system having 0-5 heteroatoms independently selected from nitrogen, oxygen, or sulfur.

In certain embodiments, the 5-6 membered monocyclic or 8-10 membered bicyclic aryl group having 0-5 heteroatoms independently selected from nitrogen, oxygen, or sulfur; the 3-8-membered saturated or partially unsaturated monocyclic ring having 0-3 heteroatoms independently selected from nitrogen, oxygen, or sulfur; or the 8-10-membered saturated or partially unsaturated bicyclic ring system having 0-5 heteroatoms independently selected from nitrogen, oxygen, or sulfur is selected from one of the following groups:

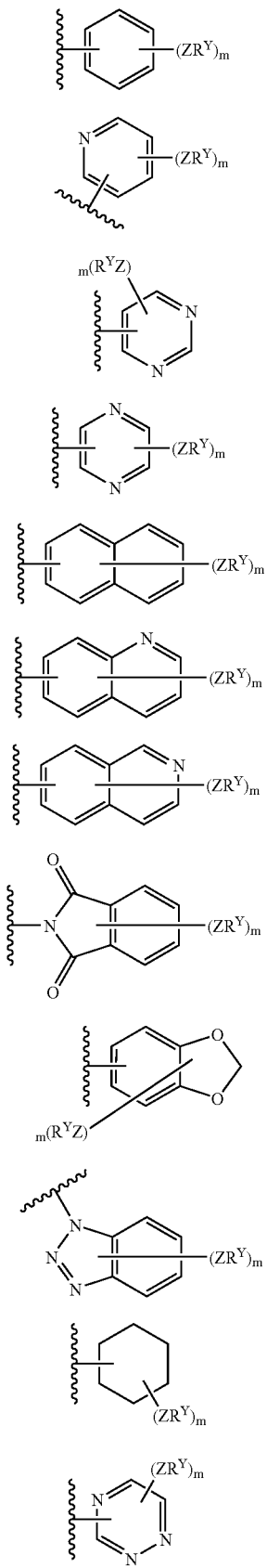
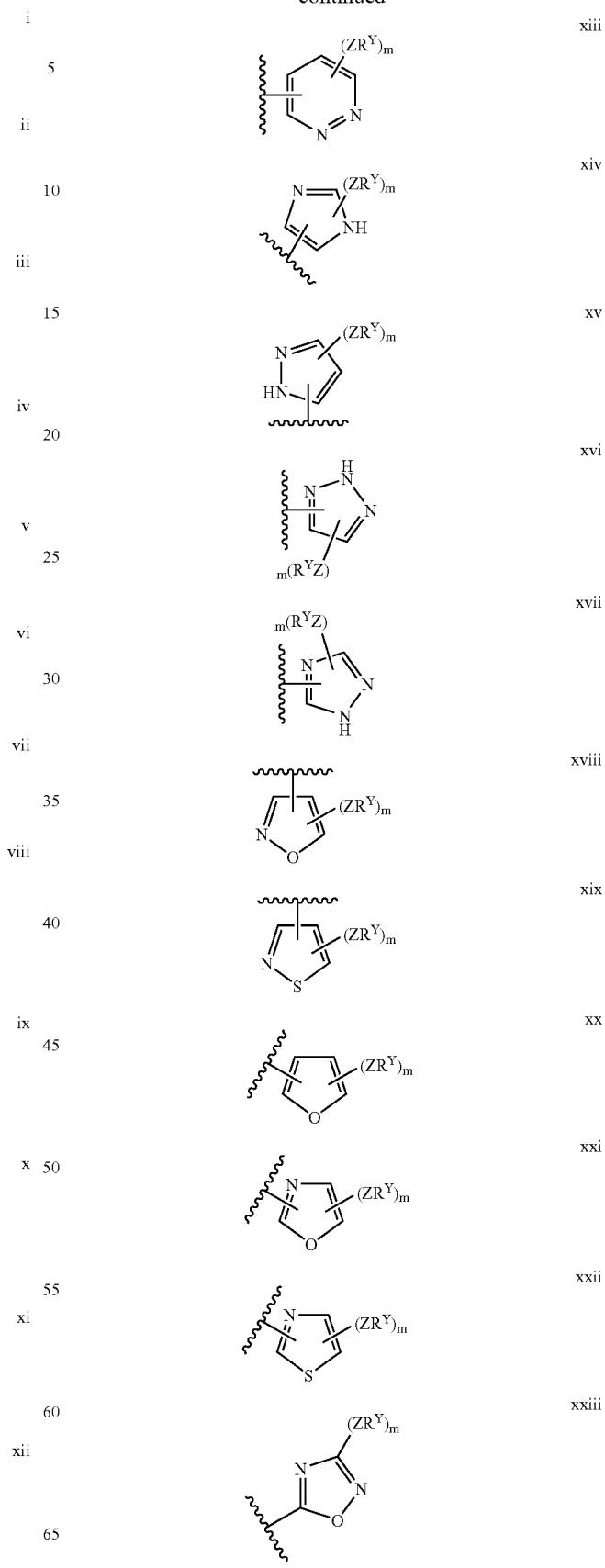

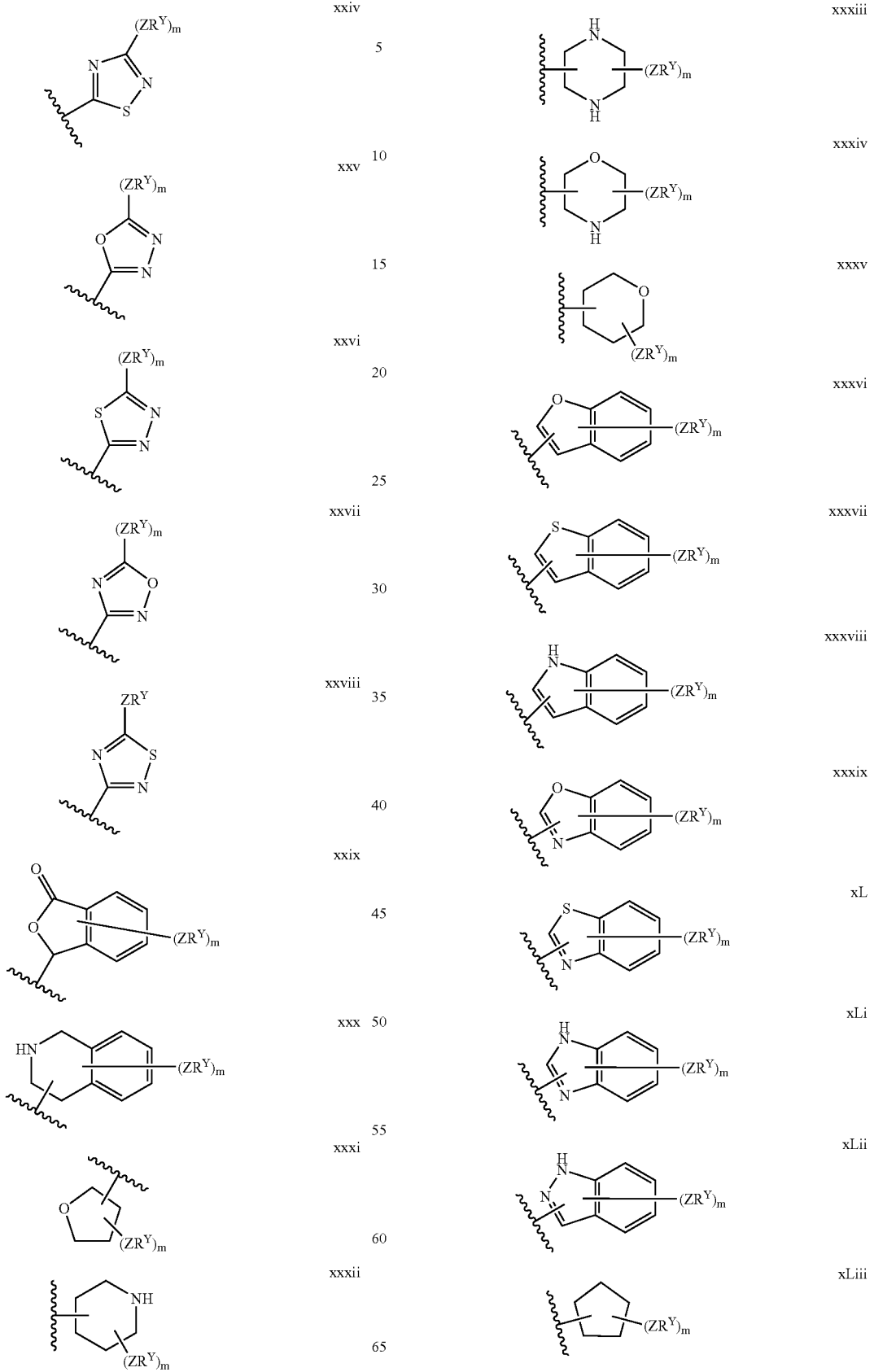

-continued

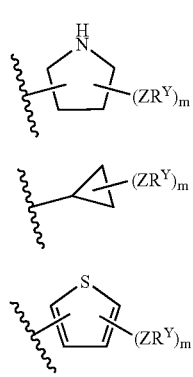

xLiv xLv xLvi

In some preferred embodiments, $R^3$ is an optionally substituted group selected from i, ii, xxxix, xL, xLi, or xLii. In other preferred embodiments, $R^3$ is an optionally substituted phenyl group (i).

It will also be appreciated that one or more hydrogen atoms on any substitutable nitrogen or carbon atom may optionally be substituted with n independent occurrences of $Z-R^Y$, wherein m is 0-5. In preferred embodiments, Z is a bond or is an optionally substituted $C_{1-6}$ alkylidene chain wherein one or two non-adjacent methylene units are optionally and independently replaced by —O—, —NR—, —S—, —$SO_2$—, or —C(O)O—, —CO—, and $R^Y$ is R' or halogen.

In other preferred embodiments, each occurrence of $ZR^Y$ is independently —$C_{1-3}$alkyl, —$O(C_{1-3}$alkyl), —OH, —$S(C_{1-3}$alkyl), —SH, $CF_3$, —$OCF_3$, —$SCF_3$, —F, —Cl, —Br, —CN, —COOR', —COR', —$O(CH_2)_2N(R')(R')$, —$O(CH_2)N(R')$ (R'), —CON(R')(R'), —NRCOR', —$(CH_2)_2OR'$, —$(CH_2)$ OR', —N(R')(R'), —$(CH_2)_2N(R')(R')$, —$(CH_2)N(R')(R')$, —$SO_2N(R')(R')$, —$NRSO_2R'$, or an optionally substituted group selected from pyrrolidinyl, morpholino, piperazinyl, piperidinyl, phenyl, phenoxy, benzyl, benzyloxy, triazolyl, pyrazolyl, or pyridyl.

In some embodiments m is 0. In other embodiments m is 1. In still other embodiments m is 2.

In preferred embodiments, any substitutable nitrogen atom is substituted with hydrogen, or an optionally substituted group selected from $C_{1-6}$alkyl, aryl, aryl($C_{1-6}$)alkyl, —N (R')$_2$, —$CH_2N(R')_2$, —$CH_2OR'$, —$CH_2SR'$, —$(CH_2)_2N$ (R')$_2$, —$(CH_2)_2OR'$, —$(CH_2)_2SR'$, —COR', —CON(R')$_2$, $SO_2R'$, or —$S(O)_2N(R')_2$. In more preferred embodiments, any substitutable nitrogen atom is substituted with H, Me, $CF_3$, ethyl, propyl, butyl, pentyl, CO($C_1$-$C_4$alkyl), —$CONH_2$, —COO($C_1$-$C_4$alkyl), —$CH_2OH$, —$SO_2(C_1$-$C_4$alkyl), —$SO_2NH_2$, $SO_2N(CH_3)_2$, or optionally substituted phenyl or benzyl.

In other preferred embodiments, compounds have the general formula I-A:

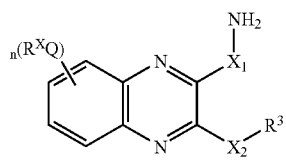

I-A wherein $X_1$, $X_2$, $R^3$, $QR^X$ and n are as described generally and in subsets above.

In some embodiments, compounds have the general formula I-A provided that
a) when n is 0, then:
   i) when $X_1$ is CO and $X_2$ is $CH_2$, then $R^3$ is not substituted furyl, 2-Cl-phenyl, 3,5-dimethyl-2-benzofuranyl, 3,7-dimethyl-2-benzofuranyl, or 4-OMe-phenyl;
   ii) when $X_1$ is CO and $X_2$ is NH, then $R^3$ is not 2,4-dichloro-phenyl, 4-Cl-phenyl, 4-Me-phenyl, or unsubstituted phenyl, cyclohexyl, or benzyl; and
   iii) when $X_1$ is CO and $X_2$ is CHOH, then $R^1$ is not unsubstituted phenyl or —$CHOHCH_2OH$; and
b) when n is 2, and the two occurrences of $QR^X$ are 6,7-Me-phenyl, then when $X_1$ is CO, and $X_2$ is NH, then $R^3$ is not n-hexyl, n-butyl, n-propyl, or —$CH_2CH=CH_2$.

In other embodiments, compounds have the general formula I-A provided that
a) when n is 0, then:
   i) when $X_1$ is CO, and $X_2$ is CH, then $R^3$ is not unsubstituted phenyl or OH;
   ii) when $X_1$ is CO, and $X_2$ is $CH_2$, then $R^3$ is not methyl, unsubstituted phenyl, substituted furyl, 2-Cl-phenyl, 3,5-dimethyl-2-benzofuranyl, 3,7-dimethyl-2-benzofuranyl, or 4-OMe-phenyl;
   iii) when $X_1$ is CO, and $X_2$ is NH, then $R^3$ is not methyl, —C(O)$CH_3$, C(O)C($C_{1-3}$alkyl), C(O)C(O)OH, C(O)C(O)O($C_{1-3}$alkyl), unsubstituted phenyl, cyclohexyl, benzyl, substituted benzofuranyl, 2,4-dichloro-phenyl, 4-Cl-phenyl, or 4-Me-phenyl;
   iv) when $X_1$ is CO, and $X_2$ is NMe, then $R^3$ is not methyl;
   v) when $X_1$ is CO, and $X_2$ is O, then $R^3$ is not methyl;
   vi) when $X_1$ is CO, and $X_2$ is CHOH, then $R^1$ is not unsubstituted phenyl or —$CHOHCH_2OH$;
b) when n is 2, then:
   i.) when $X_1$ is CO, and $X_2$ is NH
      a) and the two occurrences of $QR^X$ are 6,7-Me-phenyl, then $R^3$ is not n-hexyl, n-butyl, n-propyl, o-$CH_2CH=CH_2$, —CH=N—$CH_2CH=CH_2$, C(=O)NR, C(=O)OR wherein R is H or $C_{1-3}$ alkyl;
      b) and the two occurrences of $QR^X$ are 6-NHAc-7-Me-phenyl, then $R^3$ is not —C(=O)$CH_3$
      c) and the two occurrences of $QR^X$ are 6,7-OMe-phenyl, then $R^3$ is not C(O)C(O)OH or C(O)C(O) O($C_{1-3}$alkyl);
      d) and the two occurrences of $QR^X$ are 6,7-Cl-phenyl, then $R^3$ is not methyl or —$CH_2CH=CH_2$;
   ii.) when $X_1$ is CO, and $X_2$ is 0,
      a) and the two occurrences of $QR^X$ are 6-$NO_2$-7-F-phenyl, then $R^3$ is not methyl.

In other preferred embodiments, for compounds of formula I-A, $X_1$ is CO and $X_2$ is NR and compounds have the general structure I-A-i:

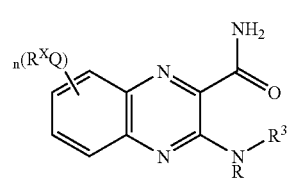

I-A-i wherein $QR^X$, R, and $R^3$ are described generally and in subsets above.

Representative examples of compounds of formula I are set forth below in Table 1.
TABLE 1
Examples of Compounds of Formula I:
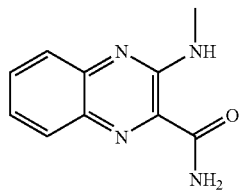
I-1
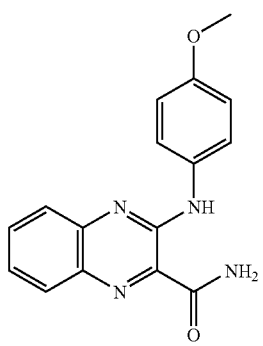
I-2
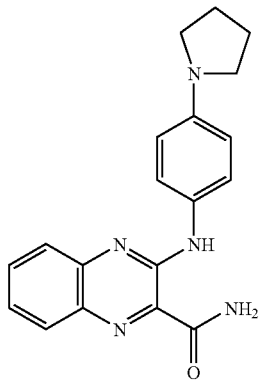
I-3
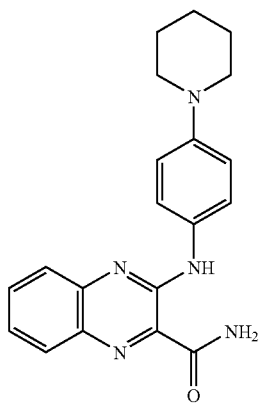
I-4
TABLE 1-continued
Examples of Compounds of Formula I:
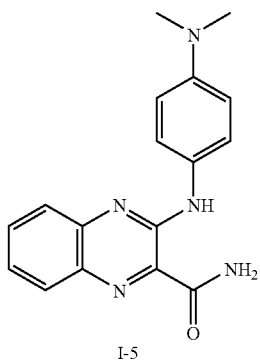
I-5
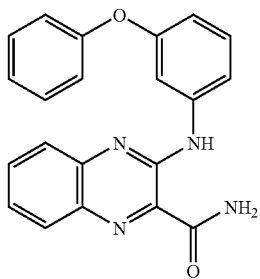
I-6
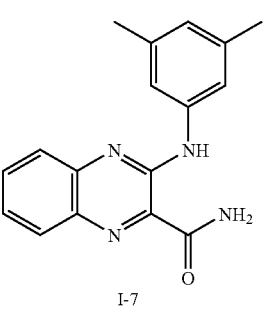
I-7
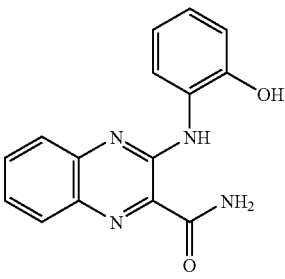
I-8
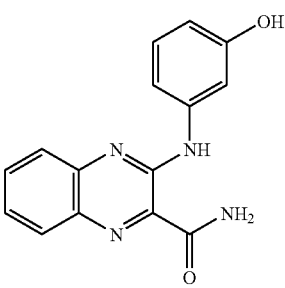
I-9

TABLE 1-continued
Examples of Compounds of Formula I:
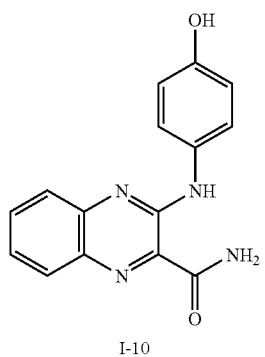
I-10
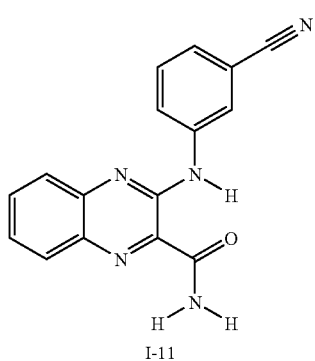
I-11
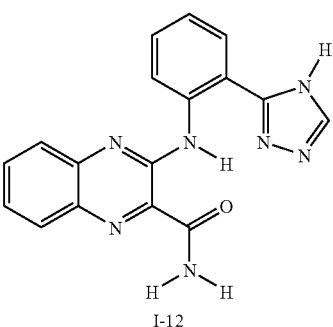
I-12
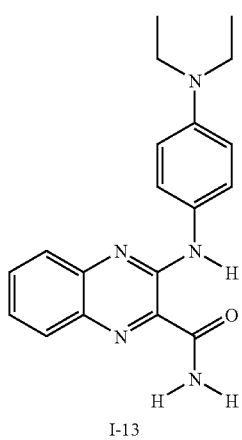
I-13
TABLE 1-continued
Examples of Compounds of Formula I:
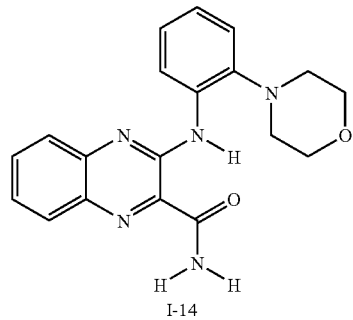
I-14
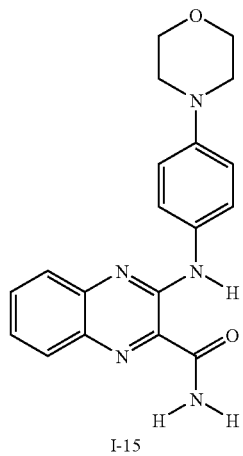
I-15
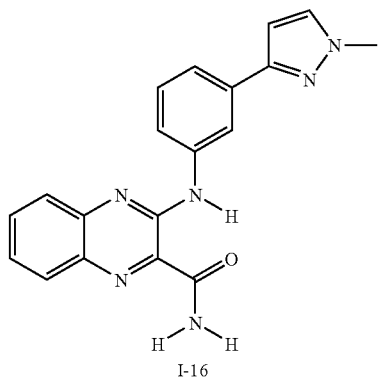
I-16
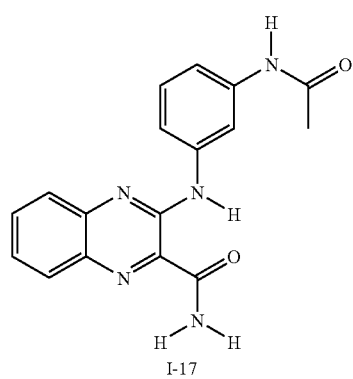
I-17

TABLE 1-continued
Examples of Compounds of Formula I:
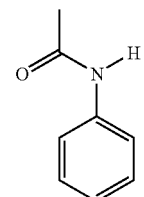
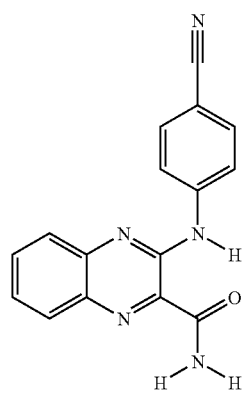
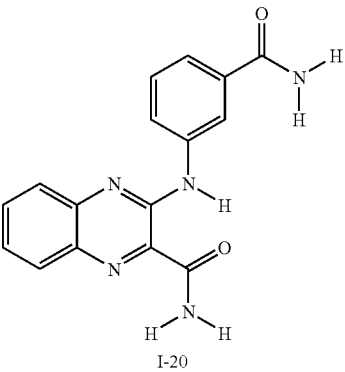
I-18
I-19
I-20
TABLE 1-continued
Examples of Compounds of Formula I:
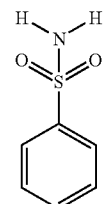
I-21
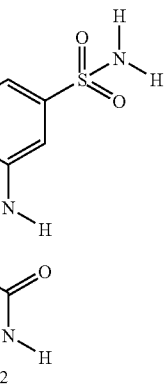
I-22
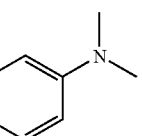
I-23
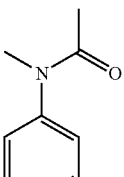
I-24

TABLE 1-continued
Examples of Compounds of Formula I:
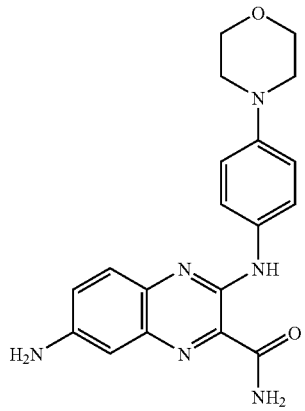
I-25
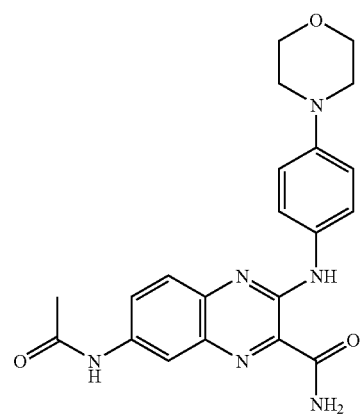
I-26
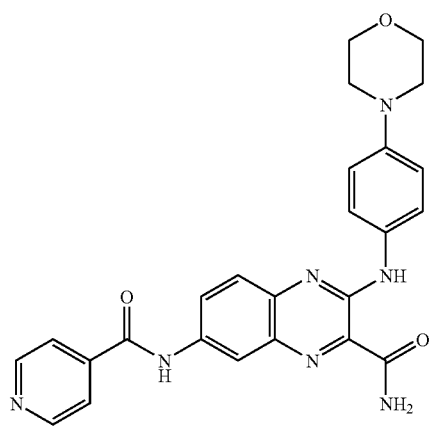
I-27
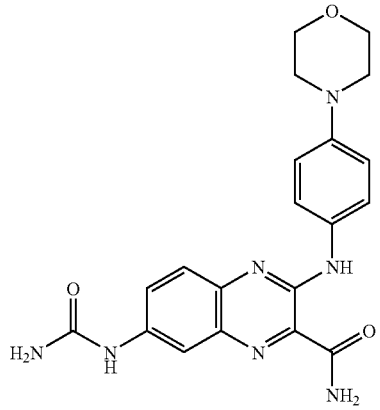
I-28
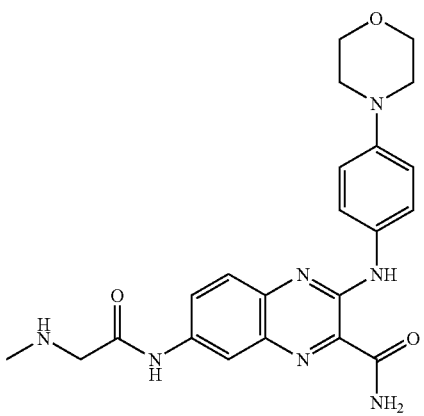
I-29
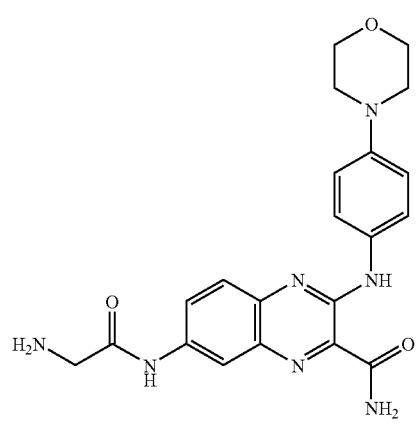
I-30

TABLE 1-continued
Examples of Compounds of Formula I:
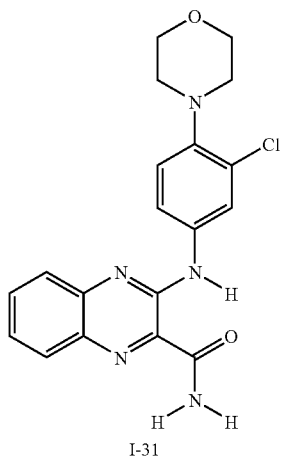
I-31
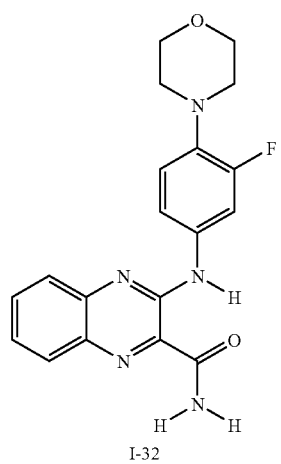
I-32
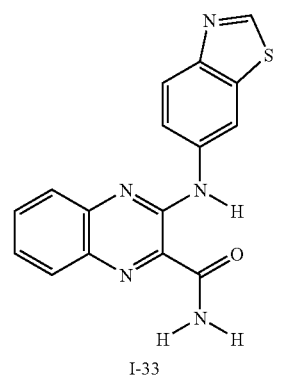
I-33
TABLE 1-continued
Examples of Compounds of Formula I:
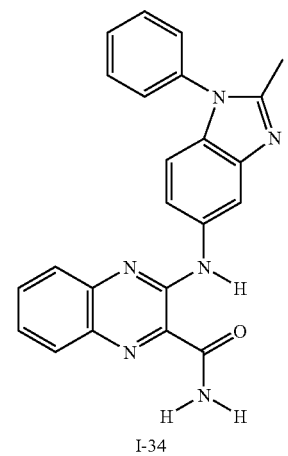
I-34
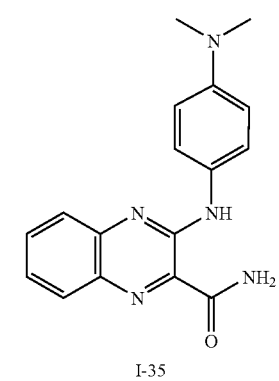
I-35
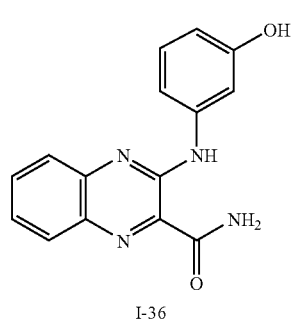
I-36
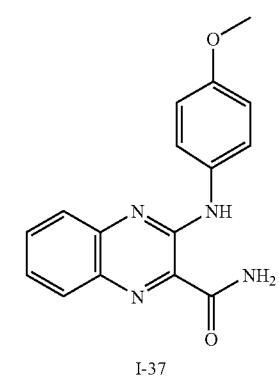
I-37

TABLE 1-continued
Examples of Compounds of Formula I:
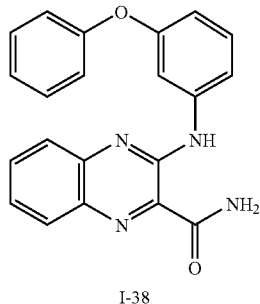
I-38
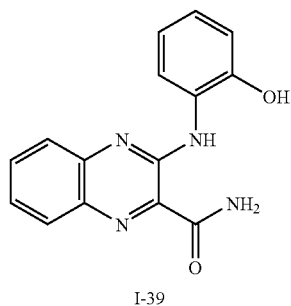
I-39
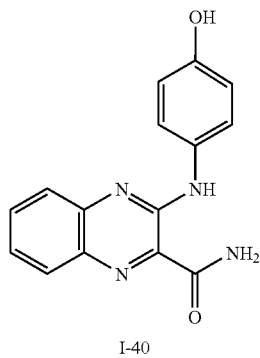
I-40
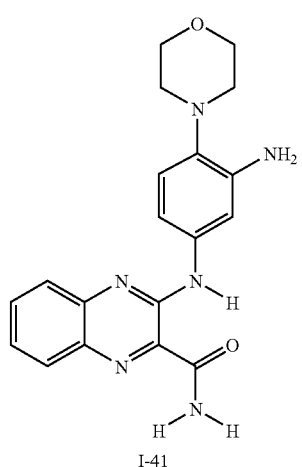
I-41
TABLE 1-continued
Examples of Compounds of Formula I:
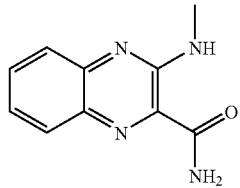
I-42
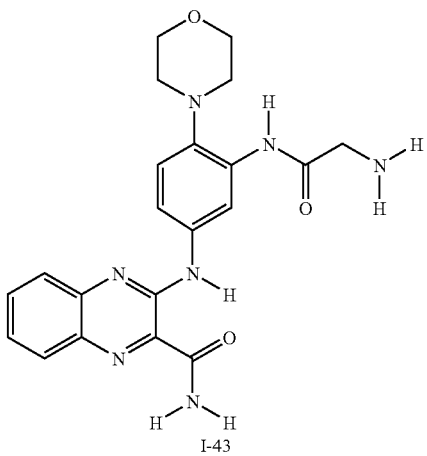
I-43
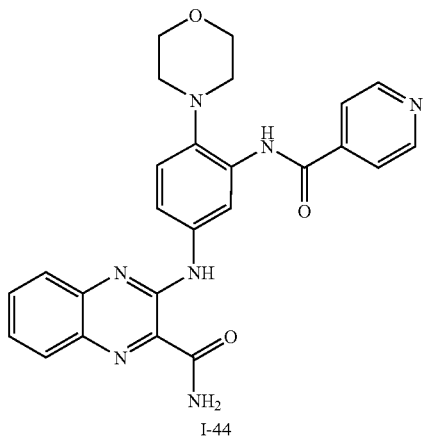
I-44
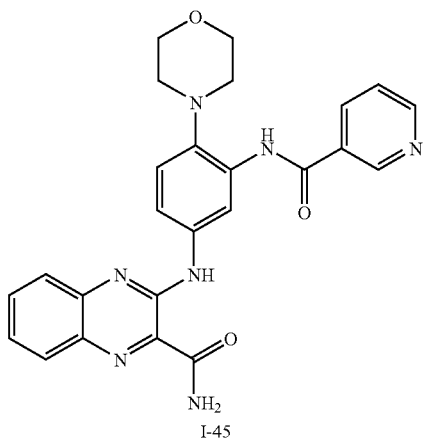
I-45

TABLE 1-continued

Examples of Compounds of Formula I:

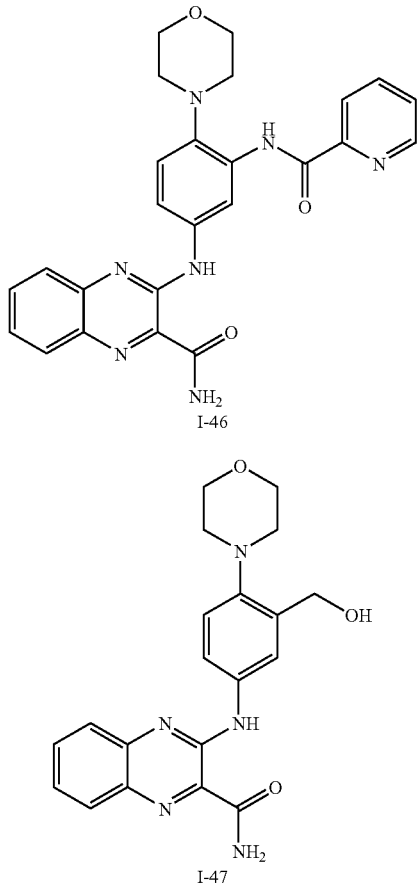

I-46

I-47

4. General Synthetic Methodology

The compounds of this invention may be prepared in general by methods known to those skilled in the art for analogous compounds or by those methods depicted in the Examples below. In general, Example 1 depicts several methods for the preparation of functionalized quinoxalines.

Although certain exemplary embodiments are depicted and described herein, it will be appreciated that a compounds of the invention can be prepared according to the methods described generally above using appropriate starting materials by methods generally available to one of ordinary skill in the art.

5. Uses, Formulation and Administration

Pharmaceutically Acceptable Compositions

As discussed above, the present invention provides compounds that are inhibitors of protein kinases, and thus the present compounds are useful for the treatment of diseases, disorders, and conditions including, but not limited to immunodeficiency disorders, inflammatory diseases, allergic diseases, autoimmune diseases, proliferative disorders, immunologically-mediated diseases, or respiratory disorders. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a SYK, JAK-3, or GSK-3 kinase.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of a proliferative disorder, a cardiac disorder, a neurodegenerative disorder, an autoimmune disorder, a condition associated with organ transplant, an inflammatory disorder, or an immunologically mediated disorder is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for treating or lessening the severity of a proliferative disorder, a cardiac disorder, a neurodegenerative disorder, an autoimmune disorder, a condition associated with organ transplant, an inflammatory disorder, or an immunologically mediated disorder. The compounds and compositions, according to the method of the present invention, may be administered using any amount and any route of administration effective for treating or lessening the severity of a proliferative disorder, a cardiac disorder, a neurodegenerative disorder, an autoimmune disorder, a condition associated with organ transplant, an inflammatory disorder, or an immunologically mediated disorder. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of protein kinases. In one embodiment, the compounds and compositions of the invention are inhibitors of one or more of SYK, JAK-3, or GSK-3, and thus, without wishing to be bound by any particular theory, the compounds and compositions are particularly useful for treating or lessening the severity of a disease, condition, or disorder where activation of one or more of SYK, JAK-3, or GSK-3 is implicated in the disease, condition, or disorder. When activation of SYK, JAK-3, or GSK-3 is implicated in a particular disease, condition, or disorder, the disease, condition, or disorder may also be referred to as "SYK, JAK-3, or GSK-3-mediated disease" or disease symptom. Accordingly, in another aspect, the present invention provides a method for treating or lessening the severity of a disease, condition, or disorder where activation or one or more of SYK, JAK-3, or GSK-3 is implicated in the disease state.

The activity of a compound utilized in this invention as an inhibitor of SYK, JAK-3, or GSK-3, may be assayed in vitro, in vivo or in a cell line. In vitro assays include assays that determine inhibition of either the phosphorylation activity or ATPase activity of activated SYK, JAK-3, or GSK-3. Alternate in vitro assays quantitate the ability of the inhibitor to bind to SYK, JAK-3, or GSK-3. Inhibitor binding may be measured by radiolabelling the inhibitor prior to binding, isolating the inhibitor/SYK, JAK-3, or GSK-3, complex and determining the amount of radiolabel bound. Alternatively, inhibitor binding may be determined by running a competition experiment where new inhibitors are incubated with SYK, JAK-3, or GSK-3 bound to known radioligands.

The term "measurably inhibit", as used herein means a measurable change in SYK, JAK-3, or GSK-3 activity between a sample comprising said composition and a SYK, JAK-3, or GSK-3 kinase and an equivalent sample comprising SYK, JAK-3, or GSK-3 kinase in the absence of said composition.

The term "GSK-3-mediated disease" as used herein, means any disease or other deleterious condition or disease in which GSK-3 is known to play a role. Such diseases or conditions include, without limitation, autoimmune diseases, inflammatory diseases, metabolic, neurological and neurodegenerative diseases, cardiovascular diseases, allergy, asthma, diabetes, Alzheimer's disease, Huntington's disease, Parkinson's disease, AIDS-associated dementia, amyotrophic lateral sclerosis (AML, Lou Gehrig's disease), multiple sclerosis (MS), schizophrenia, cardiomyocyte hypertrophy, reperfusion/ischemia, stroke, and baldness.

The term "JAK-mediated disease", as used herein means any disease or other deleterious condition in which a JAK family kinase, in particular JAK-3, is known to play a role. Such conditions include, without limitation, immune responses such as allergic or type I hypersensitivity reactions, asthma, autoimmune diseases such as transplant rejection, graft versus host disease, rheumatoid arthritis, amyotrophic lateral sclerosis, and multiple sclerosis, neurodegenerative disorders such as Familial amyotrophic lateral sclerosis (FALS), as well as in solid and hematologic malignancies such as leukemias and lymphomas.

The term "SYK-mediated disease" or "SYK-mediated condition", as used herein, means any disease or other deleterious condition in which SYK protein kinase is known to play a role. Such conditions include, without limitation, allergic disorders, especially asthma.

In other embodiments, the invention relates to a method of enhancing glycogen synthesis and/or lowering blood levels of glucose in a patient in need thereof, comprising administering to said patient a therapeutically effective amount of a composition comprising a compound of formula I. This method is especially useful for diabetic patients.

In yet another embodiment, the invention relates to a method of inhibiting the production of hyperphosphorylated Tau protein in a patient in need thereof, comprising administering to said patient a therapeutically effective amount of a composition comprising a compound of formula I. This method is especially useful in halting or slowing the progression of Alzheimer's disease.

In still another embodiments, the invention relates to a method of inhibiting the phosphorylation of β-catenin in a patient in need thereof, comprising administering to said patient a therapeutically effective amount of a composition comprising a compound of formula I. This method is especially useful for treating schizophrenia.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

Another aspect of the invention relates to inhibiting SYK, JAK-3, or GSK-3 activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of SYK, JAK-3, or GSK-3 kinase activity in a biological sample is useful for a variety of purposes that are known to one of skill in the art. Examples of such purposes include, but are not limited to, blood transfusion, organ-transplantation, biological specimen storage, and biological assays.

EXAMPLES

Example 1

Synthesis of Exemplary Compounds of the Invention

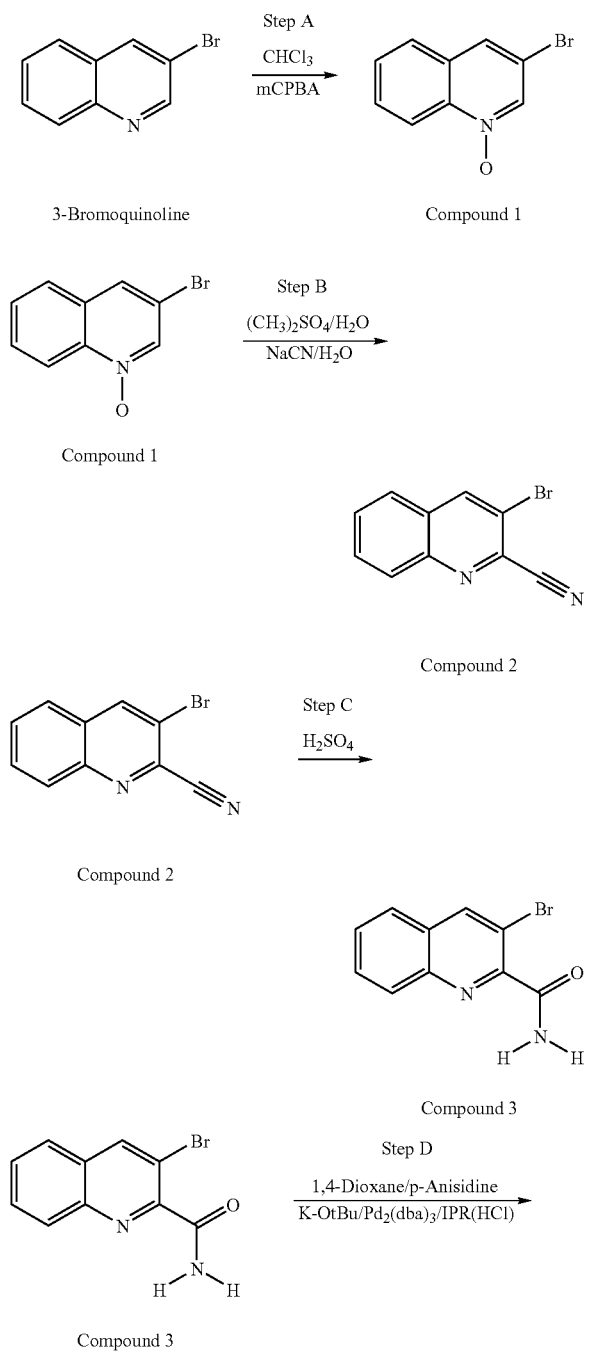

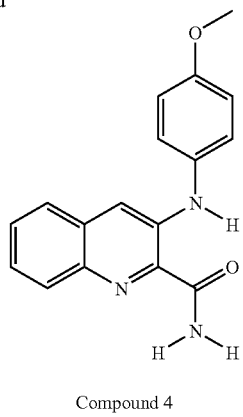

Compound 4

Step A (Compound 1)

M-CPBA (6.0 g.) was added to a solution of 3-Bromo Quinoline (4.25 g./20.4 mmol) in CHCl$_3$ (31.0 ml.). The reaction mixture was allowed to stir at room temperature overnight. The reaction mixture was diluted with saturated sodium bicarbonate solution (25 ml.) and 1N NaOH solution (7.5 ml.). The layers were separated and the aqueous layer was re-extracted with (12.5 ml) CHCl$_3$. The combined organics were washed with 5% (by weight) aqueous sodium bisulfite solution (25 ml.), saturated aqueous sodium bicarbonate solution (12.5 ml.), water (20 ml.) and brine (25 ml.). The reaction mixture was then dried over sodium sulfate, filtered and evaporated to dryness. No further purification, material used as is. Yield: 5.61 g. (impure, theoretical yield is 4.57 g.) $^1$H NMR (500 MHz, CDCl$_3$) δ 8.75 (d, 1H), 8.69 (d, 1H), 7.97 (s, 1H), 7.82-7.77 (m, 2H), 7.71-7.67 (m, 1H).

Step B (Compound 2)

A mixture of Compound 2 (20.4 mmol) and dimethyl sulfate (2.8 ml, 29.6 mmol) was heated at 70 degrees for two hours (under N$_2$). Upon cooling to room temperature, added was water (9.0 ml.) producing a precipitate. The reaction mixture was cooled to –10 degrees via an isopropanol/dry ice bath. Added was a solution of sodium cyanide (2.56 g./52.2 mmol) in water (18.0 ml.) in a dropwise manner through an addition funnel. The precipitated material was collected and recrystallized from ethyl acetate/hexane. Yield 2.33 g., approximately 50%. $^1$H NMR (500 MHz, CDCl$_3$) δ 8.51 (s, 1H), 8.15 (d, 1H), 7.88-7.83 (m, 2H), 7.76-7.73 (m, 1H).

Step C (Compound 3)

Compound 3 (800 mg., 3.45 mmol) was suspended in sulfuric acid (1.0 ml., concentrated). The reaction mixture was heated to 80 degrees where a solution occurs. After 30 minutes, the reaction mixture is allowed to cool to room temperature and is then basified with 6 N sodium hydroxide solution (with a little solid NaOH added). The product was extracted with methylene chloride, washed with water, dried over magnesium sulfate, filtered and evaporated to dryness. This crude material was recrystallized from ethyl acetate/methanol. Yield: 353.6 mg., approximately 40%. $^1$H NMR (500 MHz, CD$_3$OD) δ 8.60 (s, 1H), 7.98 (d, 1H), 7.85 (d, 1H), 7.76-7.71 (m, 1H), 7.59 (m, 1H).

Step D (Compound 4)

Compound 4 (125.6 mg./0.5 mmol) was dissolved in 1,4-dioxane (1.5 ml.). Added was p-anisidine (67.8 mg./0.55 mmol) followed by potassium tert-butoxide (180 mg./1.6 mmol.), tris (dibenzylideneacetone) dipalladium (0) (4.6 mg./0.005 mmol.) and 1,3-bis (2,6-diisopropylphenyl) imidazolium chloride (4.3 mg./0.01 mmol.). The reaction mixture was heated to 100 degrees (sealed tube, under Ar) and allowed to stir there overnight. The reaction mixture was allowed to cool to room temperature and was then diluted with ethyl acetate. This organic phase was washed with water, brine, dried over magnesium sulfate, filtered and evaporated to dryness. This crude material was chromatographed on 1.5 inches of silica gel and eluted with 1% methanol/methylene chloride. Yield: 14.1 mg. $^1$H NMR (500 MHz, CDCl$_3$) δ 8.17-7.92 (m, 2H), 7.79-7.66 (m, 1H), 7.65-7.51 (m, 2H), 7.24 (d, 2H), 6.98 (d, 2H), 6.71 (s, broad, 1H), 3.89 (s, 3H).

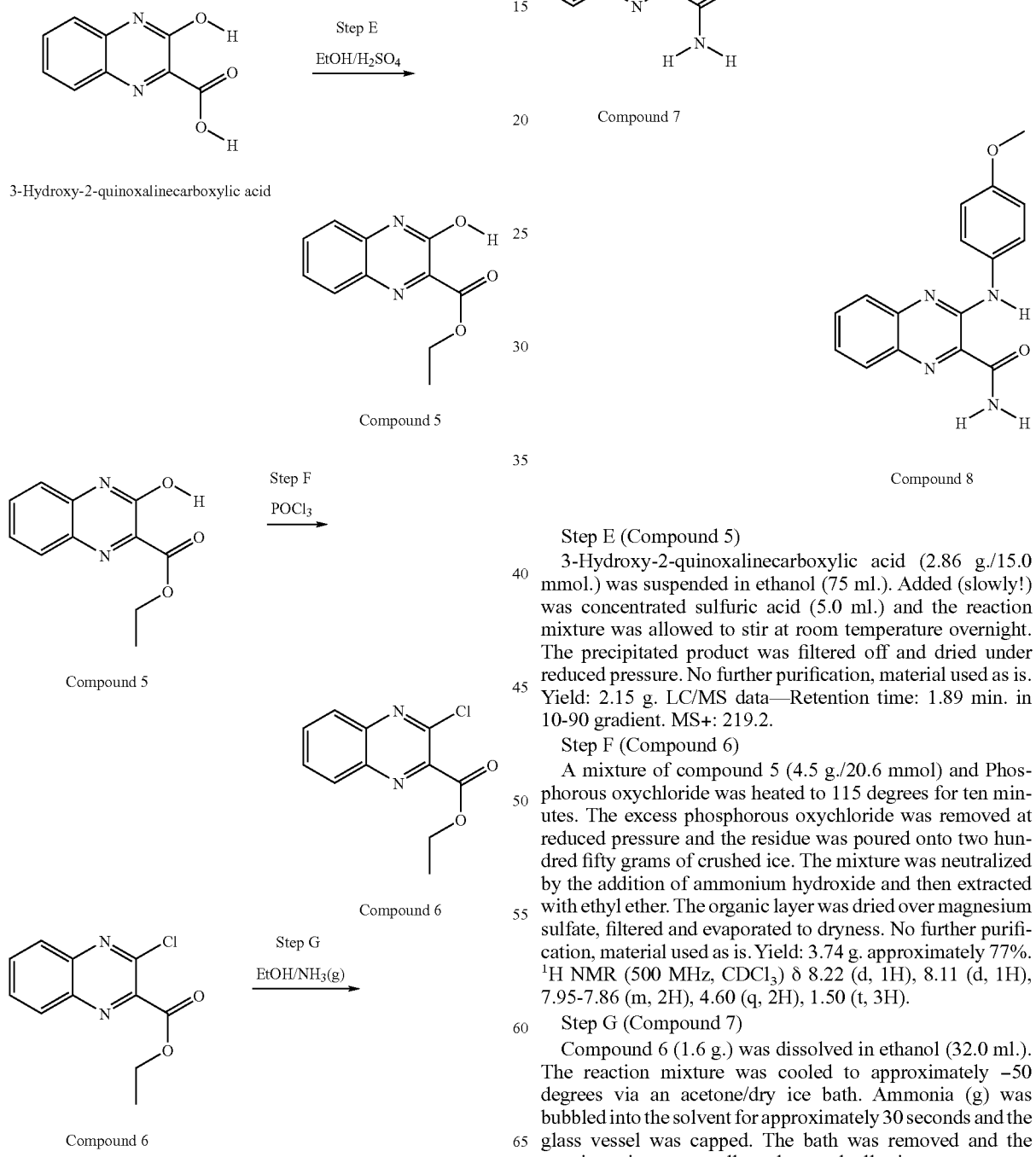

Step E (Compound 5)

3-Hydroxy-2-quinoxalinecarboxylic acid (2.86 g./15.0 mmol.) was suspended in ethanol (75 ml.). Added (slowly!) was concentrated sulfuric acid (5.0 ml.) and the reaction mixture was allowed to stir at room temperature overnight. The precipitated product was filtered off and dried under reduced pressure. No further purification, material used as is. Yield: 2.15 g. LC/MS data—Retention time: 1.89 min. in 10-90 gradient. MS+: 219.2.

Step F (Compound 6)

A mixture of compound 5 (4.5 g./20.6 mmol) and Phosphorous oxychloride was heated to 115 degrees for ten minutes. The excess phosphorous oxychloride was removed at reduced pressure and the residue was poured onto two hundred fifty grams of crushed ice. The mixture was neutralized by the addition of ammonium hydroxide and then extracted with ethyl ether. The organic layer was dried over magnesium sulfate, filtered and evaporated to dryness. No further purification, material used as is. Yield: 3.74 g. approximately 77%. $^1$H NMR (500 MHz, CDCl$_3$) δ 8.22 (d, 1H), 8.11 (d, 1H), 7.95-7.86 (m, 2H), 4.60 (q, 2H), 1.50 (t, 3H).

Step G (Compound 7)

Compound 6 (1.6 g.) was dissolved in ethanol (32.0 ml.). The reaction mixture was cooled to approximately −50 degrees via an acetone/dry ice bath. Ammonia (g) was bubbled into the solvent for approximately 30 seconds and the glass vessel was capped. The bath was removed and the reaction mixture was allowed to gradually rise to room temperature where it was stirred overnight. The reaction mixture was re-cooled to −50 degrees (as above) and the glass vessel was opened. After allowing to warm to room temperature, the solid product was collected by filtration. After washing with a small amount of cool ethanol, the product was dried under reduced pressure. Yield: 720 mg., approximately 52%. $^1$NMR (500 MHz, CDCl$_3$) δ 8.16 (d, 1H), 8.08 (d, 1H), 7.97-7.87 (m, 2H).

Step H (Compound 8)

Compound 7 (62.3 mg./0.30 mmol.) and p-Anisidine (36.4 mg./0.296 mmol.) were dissolved in pyridine (1.5 ml.). The reaction mixture was heated to 125 degrees (in a sealed tube, under N$_2$) and allowed to stir there overnight. The excess pyridine was removed with heat and a stream of N$_2$. The residue was chromatographed on a plug of silica gel (1.75 inches) and eluted with 10-25% ethyl acetate/hexane. Yield: 25.4 mg., approximately 30%. $^1$NMR (500 MHz, CDCl$_3$) δ 10.97 (s, broad, 1H), 8.19 (s, broad, 1H), 7.82 (m, 3H), 7.75 (d, 1H), 7.69 (t, 1H), 7.44 (t, 1H), 6.96 (d, 2H), 5.72 (s, broad, 1H), 3.87 (s, 3H).

Step I (Compound 9):

Scheme C:

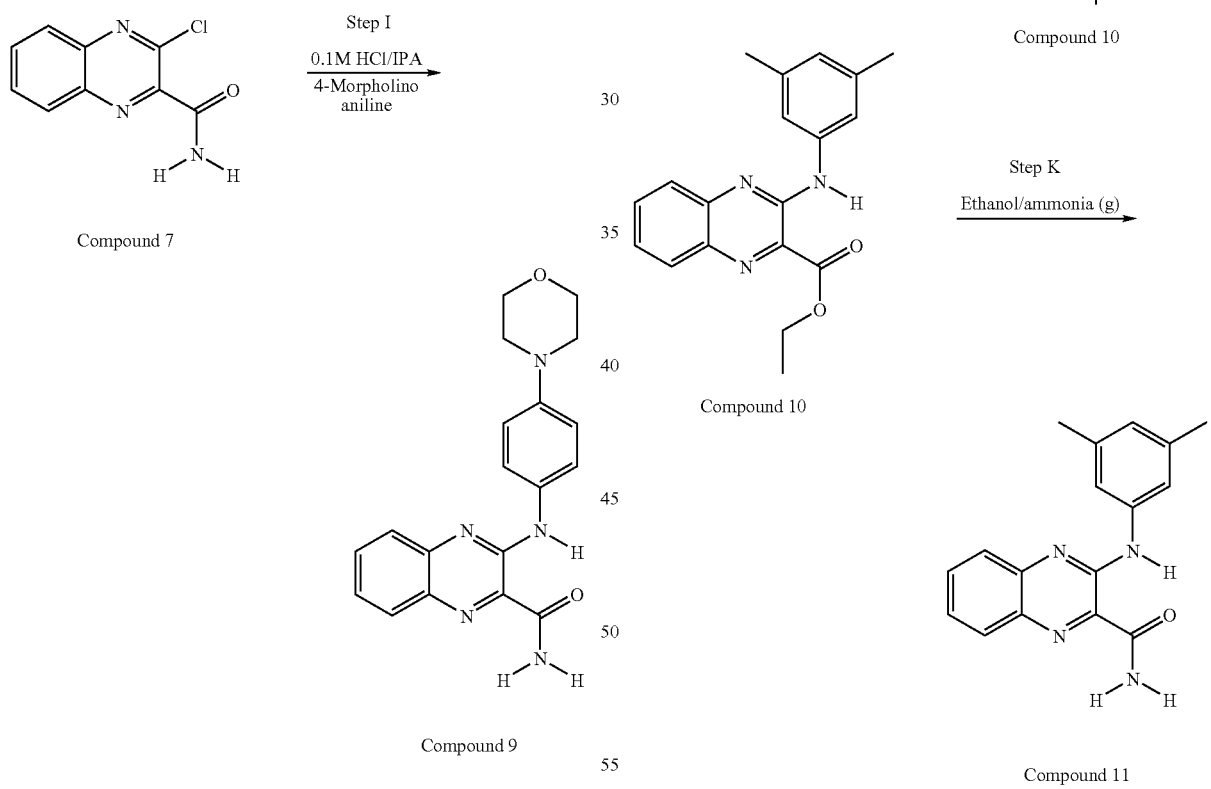

Compound 7 (64.2 mg./0.31 mmol.) and 4-Morpholino aniline (57.8 mg./0.32 mmol). were dissolved in 0.1M HCl/Isopropanol (total of 3.0 ml.). The reaction mixture was 85 degrees and allowed to stir there ovenight. After cooling to room temperature, the precipitated material was filtered, washed with ethyl ether, collected and dried under reduced pressure. This crude material was then recrystallized from methanol/ethyl acetate to give the HCl salt of the product. Yield: 25.6 mg. approximately 22%. $^1$H NMR (500 MHz, DMSO d-6)

Scheme D:

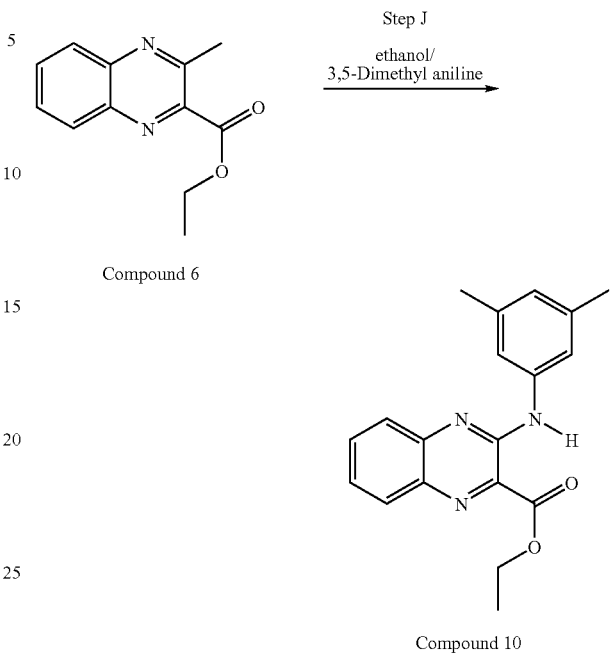

Step J (Compound 10):

Compound 6 (77.7 mg./0.33 mmol.) was dissolved in ethanol. Added was 3,5-Dimethyl aniline and the reaction mixture (in a sealed tube) was heated to 85 degrees. After stirring overnight, the reaction was allowed to cool to room temperature. The precipitated solid was diluted with ethanol and collected by filtration. Yield: 33.7 mg. approximately 30%. LC Data-retention time: 7.166 min., >95% pure, MS+(FIA) Data: 322.1.

Step K (Compound 11)

Compound 10 (33.7 mg./0.10 mmol.) was suspended in ethanol. The reaction mixture was cooled to approximately −50 degrees via an isopropanol/dry ice bath. Ammonia (g) was bubbled in for approximately 30 seconds and the vessel was capped. The reaction mixture was allowed to gradually warm to room temperature and stirred there for two hours. After re-cooling to −50 degrees, the sealed vessel was opened. Upon reaching room temperature, the precipitated solid was filtered and washed with ethanol. Yield: 24.5 mg. approximately 84%. 1H NMR (500 MHz, CDCl$_3$).

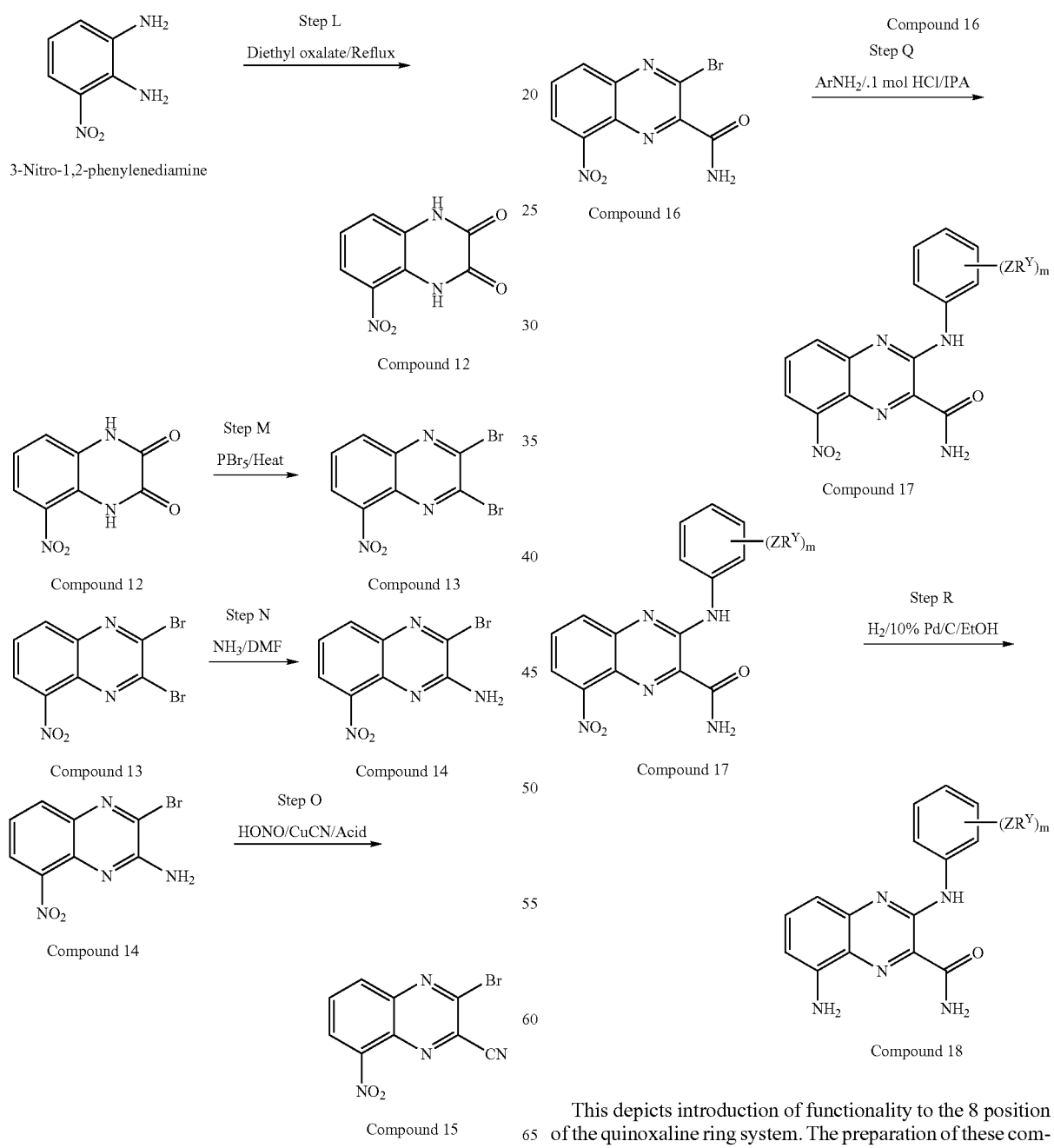

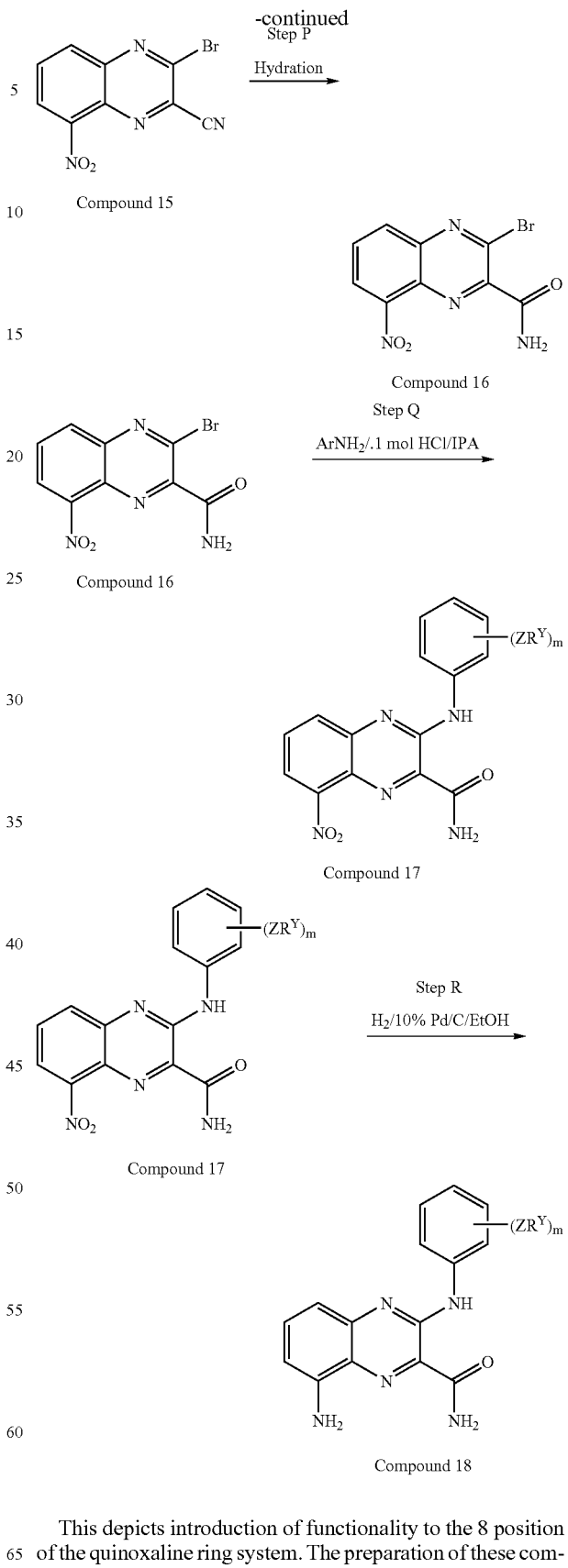

This depicts introduction of functionality to the 8 position of the quinoxaline ring system. The preparation of these compounds is analogous to those of Li and Yue in Tetrahedron Letters, Volume 40 (1999) pp. 4507–4510 and preparations described herein. The nitro group may be reduced at selected steps along the way to the amino compound, which may be further diversified by diazotization and subsequent replacement of the diazonium salt.
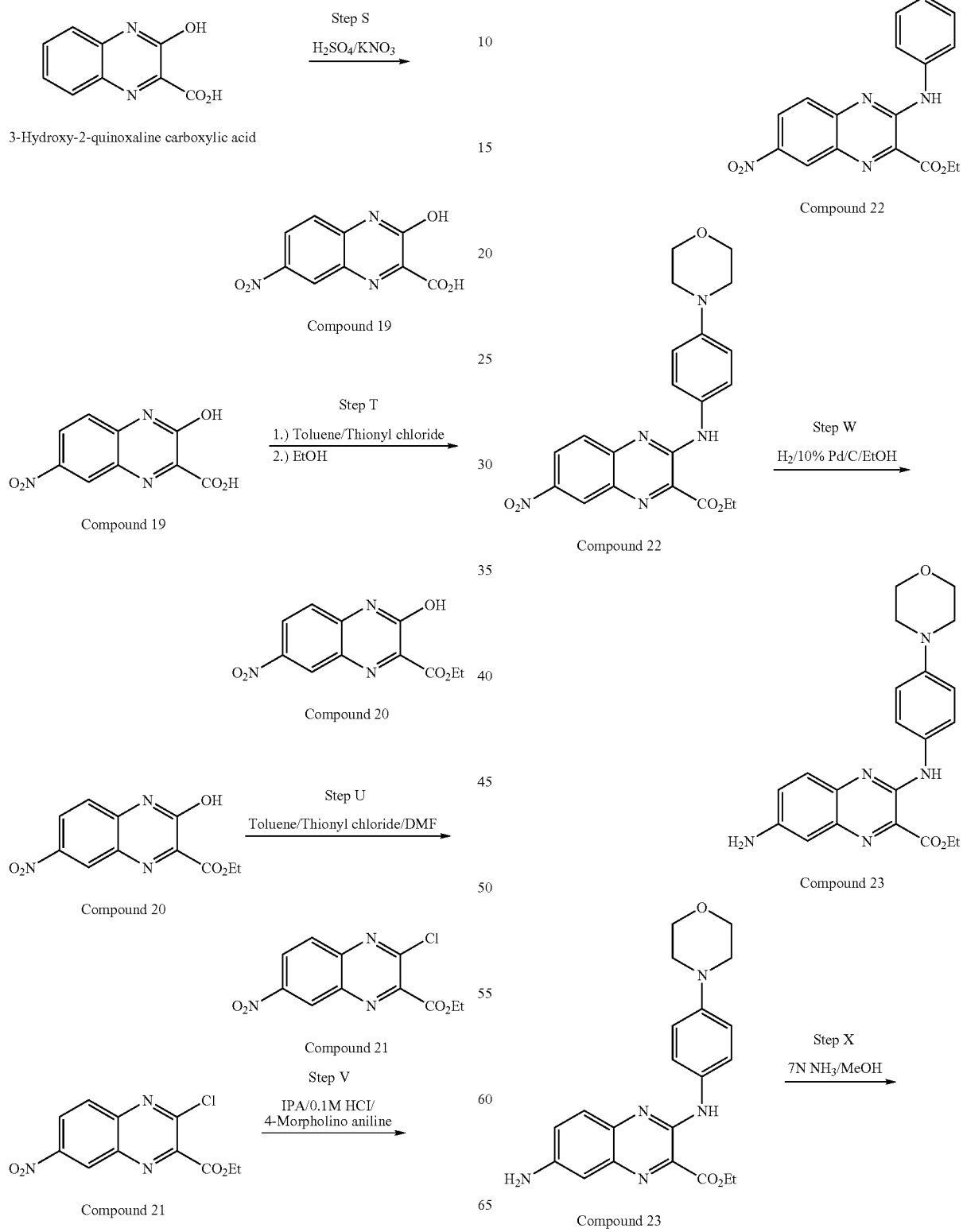

-continued

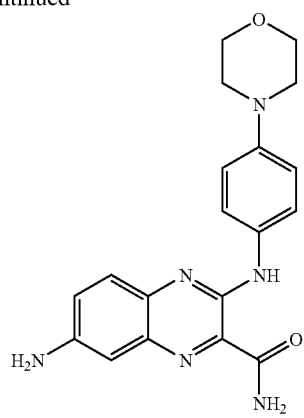

Compound 24

Step S (Compound 19)

3-Hydroxy-2-quinoxaline carboxylic acid (15.0 g/78.9 mmol) was dissolved in concentrated sulfuric acid (225 ml). The reaction mixture was cooled in an ice—water bath and added slowly was Potassium nitrate (24.0 g/237.4 mmol). After completion of addition, the cooling bath was removed and the reaction mixture was allowed to reach room temperature where it was stirred overnight. The reaction mixture was poured onto ice (900 g) and the resulting precipitate was filtered. The solid was dissolved in boiling water (2.4 L) and filtered hot. Upon cooling to room temperature, the precipitated product was collected by filtration and washed with $Et_2O$. Yield: 11.40 g (62%, approximately) $^1H$ NMR (500 MHz, DMSO-d6) δ 8.61 (s, 1H), 8.46 (d, 1H), 7.50 (s, 1H).

Step T (Compound 20)

Compound 19 (6.65 g/28.3 mmol) was suspended in toluene (250 ml). Added was thionyl chloride (25 ml/342.7 mmol) and the resulting reaction mixture was heated to reflux (under N2). After 2 hours all volatiles were removed at reduced pressure. The residue was suspended in ethanol (250 ml) and brought to reflux (under $N_2$), where it was allowed to stir overnight. All volatiles were removed at reduced pressure and the residue was recrystallized from ethanol. Yield: 2.85 g (38%, approximately). $^1H$ NMR (500 MHz, DMSO-d6) δ 8.62 (s, 1H), 8.48 (d, 1H), 7.49 (d, 1H), 4.39 (q, 2H), 1.33 (t, 3H).

Step U (Compound 21)

Compound 20 (2.85 g/10.83 mmol) was suspended in toluene (45 ml). Added was thionyl chloride (1.0 ml/13.7 mmol) followed by DMF (1.0 ml). The reaction mixture is heated to reflux and allowed to stir there for 2 hours. All volatiles were removed at reduced pressure and the residue was recrystallized from EtOAc/Hexane. Yield: 3.1 g (assume quantitative, slightly impure). $^1H$ NMR (500 MHz, DMSO-d6) δ 9.09 (s, 1H), 8.66 (d, 2H), 8.22 (d, 2H), 4.61 (q, 2H), 1.49 (t, 3H).

Step V (Compound 22)

Compound 21 (2.26 g/8.0 mmol) and 4-morpholino aniline (1.5 g/8.4 mmol) were suspended in 0.1 M HCl/Isopropanol (80 ml). The reaction mixture was heated to reflux and allowed to stir there for 1 hour. After cooling to room temperature, the product was filtered and collected. The product was washed with $Et_2O$ and pumped down overnight. The product was taken up in boiling methanol (approximately 100 ml) and allowed to cool to room temperature. The product was then collected and washed with $Et_2O$. Yield: 1.70 g (50%, approximately). $^1H$ NMR (500 MHz, DMSO-d6) δ 10.29 (s, br, 1H), 8.72 (s, 1H), 8.46 (d, 1H), 7.83 (m, 3H), 7.20 (s, br, 2H), 4.50 (q, 2H), 3.82 (s, br, 4H), 3.25 (s, br, 4H), 1.41 (t, 3H).

Step W (Compound 23)

Compound 22 (1.70 g/4.0 mmol) and 10% Palladium on carbon (170 mg) were suspended in ethanol (50 ml). Added via balloon was hydrogen gas. After 1 hour, TLC indicates all of starting material to have been consumed. The reaction mixture was filtered and all volatiles were removed at reduced pressure. No further purification, material used as is. Yield: 1.39 g (88%, approximately). $^1H$ NMR (500 MHz, DMSO-d6) δ 9.76 (s, br, 1H), 7.77 (d, 1H), 7.58 (d, 1H), 7.37 (d, 2H), 7.17-7.02 (m, 3H), 6.73 (s, br, 1H), 6.51 (s, br, 1H), 4.46 (q, 2H), 3.83-3.72 (m, 4H), 3.21-3.10 (m, 4H), 1.40 (t, 3H).

Step X (Compound 24)

Compound 23 (1.39 g/3.5 mmol) was dissolved in MeOH (10 ml) and 7N $NH_3$/MeOH solution (10 ml). The reaction mixture was capped and heated to 70 degrees C. After 1 hour, TLC indicates some starting material still present. Added was another (10 ml) portion of 7N $NH_3$/MeOH, the tube was recapped and heating at 70 degrees C. was continued for 1 more hour. All volatiles were removed at reduced pressure. The residue was taken up in boiling methanol and allowed to cool to room temperature. The product was filtered and washed with $Et_2O$. Yield: 600 mg. (47%, approximately). $^1H$ NMR (500 MHz, DMSO-d6)

Scheme G:

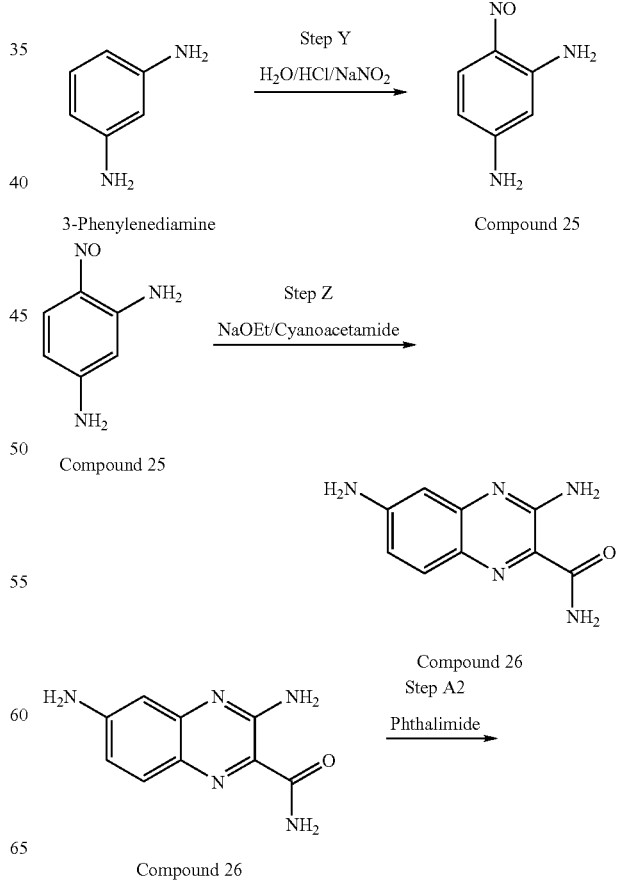

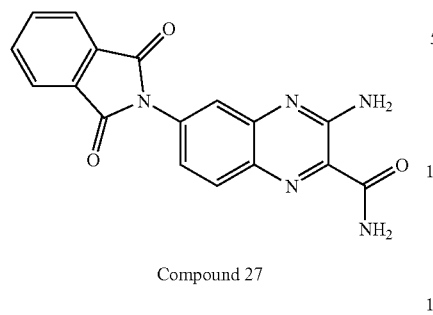

Compound 27

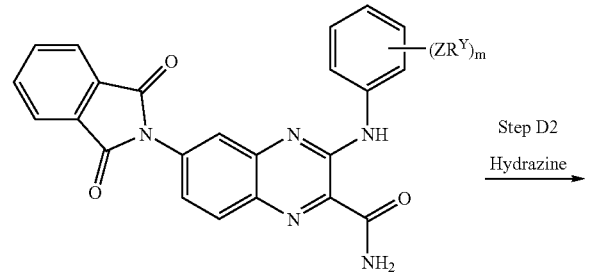

Compound 29

Step D2
Hydrazine

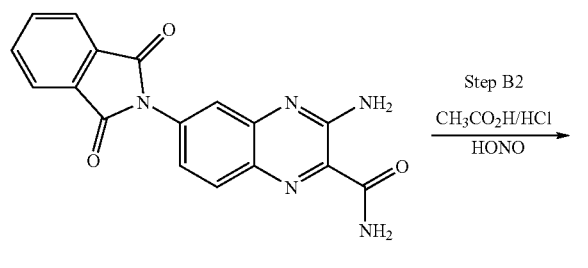

Compound 27

Step B2
CH₃CO₂H/HCl
HONO

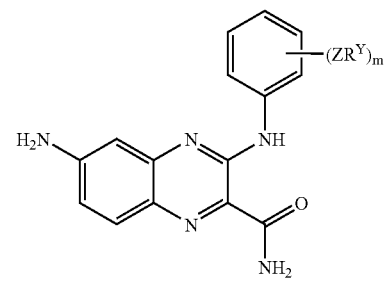

Compound 30

This scheme depicts the introduction of functionality to the 6 position of the quinoxaline ring system. The preparation of these compounds is analogous to those of Osdene and Timmis in the Journal of the Chemical Society (1955) pp. 2027-2031 and preparations described herein. The 6-amino compound may be further diversified by diazotization and subsequent replacement of the diazonium salt.

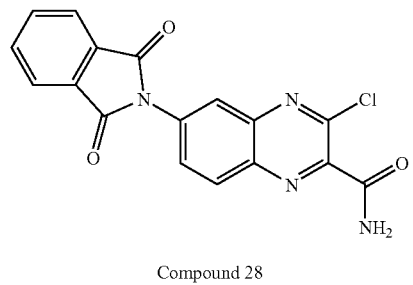

Compound 28

Scheme H:

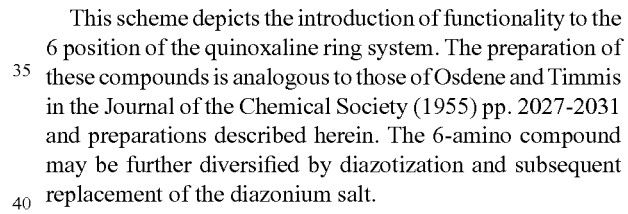

2,6-Dinitro aniline

Step E2
Toluene/Ethyl malonyl chloride

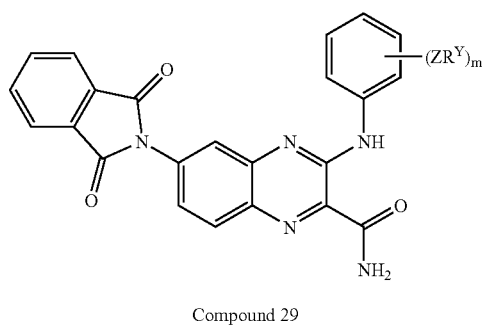

Compound 28

Step C2
ArNH₂/
0.1M HCl/
IPA

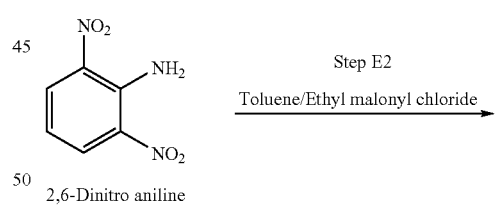

Compound 31

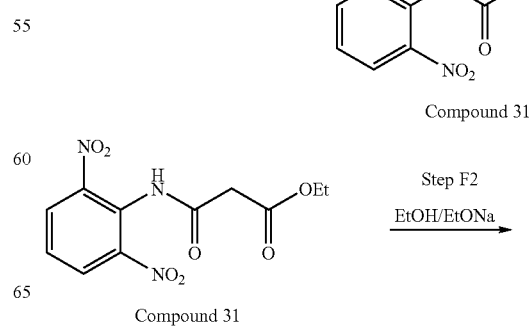

Compound 29

Compound 31

Step F2
EtOH/EtONa

-continued

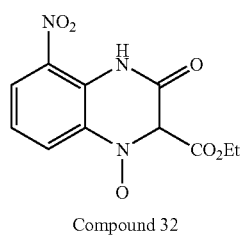
Compound 32

Step G2
PCl₃/THF

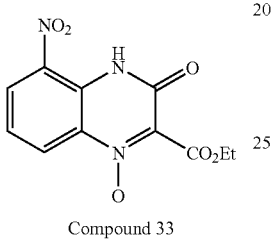
Compound 32

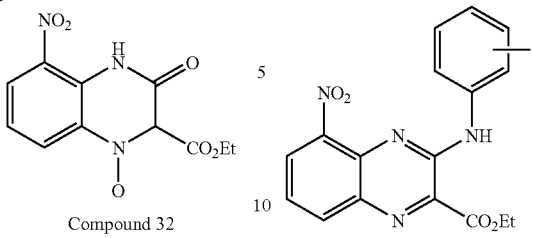
Compound 35

Step J2
H₂/Pd/C/EtOH

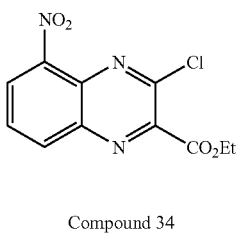
Compound 33

Step H2
POCl₃

Compound 33

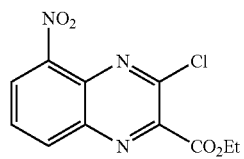
Compound 34

Step I2
ArNH₂/0.1M HCl /IPA

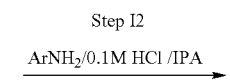
Compound 34

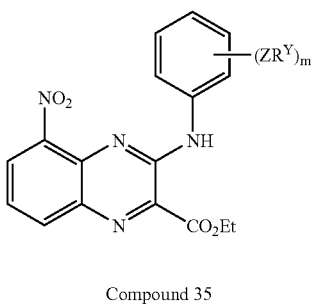
Compound 35

Compound 36

Compound 36

Step K2
7N NH₃/MeOH/MeOH

Compound 37

This scheme depicts the introduction of functionality to the 5 position of the quinoxaline ring system. The preparation of these compounds is analogous to those of U.S. Pat. No. 4,264,600 and preparations described herein. The nitro group may be reduced at selected steps along the way to the amino compound, which may be further diversified by diazotization and subsequent replacement of the diazonium salt.

Example 2

GSK-3 Inhibition Assay

Compounds of the present invention were screened for their ability to inhibit GSK-3β (AA 1-420) activity using a standard coupled enzyme system (Fox et al., *Protein Sci.* 1998, 7, 2249). Reactions were carried out in a solution containing 100 mM HEPES (pH 7.5), 10 mM MgCl₂, 25 mM NaCl, 300 μM NADH, 1 mM DTT and 1.5% DMSO. Final substrate concentrations in the assay were 20 µM ATP (Sigma Chemicals, St Louis, Mo.) and 300 µM peptide (American Peptide, Sunnyvale, Calif.). Reactions were carried out at 30° C. and 20 nM GSK-3β. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above with the exception of ATP and the test compound of the present invention. The assay stock buffer solution (175 µl) was incubated in a 96 well plate with 5 µl of the test compound of the present invention at final concentrations spanning 0.002 µM to 30 µM at 30° C. for 10 min. Typically, a 12 point titration was conducted by preparing serial dilutions (from 10 mM compound stocks) with DMSO of the test compounds of the present invention in daughter plates. The reaction was initiated by the addition of 20 µl of ATP (final concentration 20 µM). Rates of reaction were obtained using a Molecular Devices Spectramax plate reader (Sunnyvale, Calif.) over 10 min at 30° C. The $K_i$ values were determined from the rate data as a function of inhibitor concentration. Compounds of the invention were found to inhibit GSK-3.

Example 3

JAK3 Inhibition Assay

Compounds were screened for their ability to inhibit JAK using the assay shown below. Reactions were carried out in a kinase buffer containing 100 mM HEPES (pH 7.4), 1 mM DTT, 10 mM $MgCl_2$, 25 mM NaCl, and 0.01% BSA.

Substrate concentrations in the assay were 5 µM ATP (200 uCi/umole ATP) and 1 µM poly(Glu)$_4$Tyr. Reactions were carried out at 25° C. and 1 nM JAK3.

To each well of a 96 well polycarbonate plate was added 1.5 ul of a candidate JAK3 inhibitor along with 50 ul of kinase buffer containing 2 uM poly(Glu)$_4$Tyr and 10 uM ATP. This was then mixed and 50 ul of kinase buffer containing 2 nM JAK3 enzyme was added to start the reaction. After 20 minutes at room temperature (25 C), the reaction was stopped with 50 ul of 20% trichloroacetic acid (TCA) that also contained 0.4 mM ATP. The entire contents of each well were then transferred to a 96 well glass fiber filter plate using a TomTek Cell Harvester. After washing, 60 ul of scintillation fluid was added and 33P incorporation detected on a Perkin Elmer TopCount. Compounds of the invention were found to inhibit JAK-3.

Example 4

JAK2 Inhibition Assay

As above (for JAK3) except that final poly(Glu)$_4$Tyr concentration is 15 uM and final ATP concentration is 12 uM. Compounds of the invention were found to inhibit JAK-2.

Example 5

SYK Inhibition Assay

Compounds were screened for their ability to inhibit SYK using a standard coupled enzyme assay (Fox et al., *Protein Sci.* 1998, 7, 2249). Reactions were carried out in 100 mM HEPES (pH 7.5), 10 mM $MgCl_2$, 25 mM NaCl, 1 mM DTT and 1.5% DMSO. Final substrate concentrations in the assay were 200 µM ATP (Sigma chemical Co.) and 4 µM poly Gly-Tyr peptide (Sigma Chemical Co.). Assays were carried out at 30° C. and 200 nM SYK. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above, with the exception of SYK, DTT, and the test compound of interest of the present invention. 56 µl of the test reaction was placed in a 96 well plate followed by the addition of 1 µl of 2 mM DMSO stock containing the test compound of the present invnetion (final compound concentration 30 µM). The plate was pre-incubated for ~10 minutes at 30° C. and the reaction initiated by the addition of 10 µl of enzyme (final concentration 25 nM). Rates of reaction were obtained using a BioRad Ultramark plate reader (Hercules, Calif.) over a 5 minute read time at 30° C., and $K_i$ values for the compounds of the present invention were determined according to standard methods. Compounds of the invention were found to inhibit SYK.

The invention claimed is:

1. A compound of formula (I):

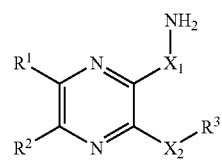

or a pharmaceutically acceptable salt thereof, wherein:
$R^1$ and $R^2$, taken together, form an optionally substituted 6-membered monocyclic aryl ring optionally substituted at one or more substitutable carbon atoms with n independent occurrences of Q-$R^x$, wherein n is 0-5;
each occurrence of R is independently selected from hydrogen or an optionally substituted $C_{1-6}$ aliphatic group; and each occurrence of R' is independently hydrogen or an optionally substituted group selected from $C_{1-8}$ aliphatic; a 5-6 membered monocyclic or an 8-10 membered bicyclic aryl group having 0-5 heteroatoms independently selected from nitrogen, oxygen, or sulfur; a 3-8-membered saturated or partially unsaturated monocyclic ring having 0-3 heteroatoms independently selected from nitrogen, oxygen, or sulfur; or an 8-10-membered saturated or partially unsaturated bicyclic ring system having 0-5 heteroatoms independently selected from nitrogen, oxygen, or sulfur;
each independent occurrence of Q is a bond or is a $C_1$-$C_6$ alkylidene chain wherein up to two methylene units of Q are optionally replaced by —C(O)—, —C(S)—, —C(O)C(O)—, —C(O)NR—, —C(O)NRNR—, —$C_2$—, —OC(O)—, —NRCO$_2$—, —O—, —NRC(O)NR—, —OC(O)NR—, —NRNR, —NRC(O)—, —S—, —SO—, —SO$_2$—, —NR—, —SO$_2$NR—, or —NRSO$_2$—; and each occurrence of $R^x$ is independently R', halogen, NO$_2$, or CN;
$X_1$ is C=O, S=O, SO$_2$, or C=NR;
$X_2$ is NR, S, O, or C(R)$_2$; and
$R^3$ is an optionally substituted group selected from: $C_{1-6}$ aliphatic; a 5-6 membered monocyclic or an 8-10 membered bicyclic aryl group having 0-5 heteroatoms independently selected from nitrogen, oxygen, or sulfur; a 3-8-membered saturated or partially unsaturated monocyclic ring having 0-3 heteroatoms independently selected from nitrogen, oxygen, or sulfur; or an 8-10- membered saturated or partially unsaturated bicyclic ring system having 0-5 heteroatoms independently selected from nitrogen, oxygen, or sulfur, wherein $R^3$ is optionally substituted with m independent occurrences of $Z$-$R^Y$, wherein m is 0-5; each independent occurrence of Z is a bond or is a $C_1$-$C_6$ alkylidene chain, wherein up to two methylene units of Z are optionally replaced by —C(O)—, —C(O)C(O)—, —C(O)NR—, —C(O)NRNR—, —CO$_2$—, —OC(O)—, —NRC(O)O—, —O—, —NRC(O)NR—, —OC(O)NR—, —NRNR—, —NRC(O)—, —S—, —SO—, —SO$_2$—, —NR—, —SO$_2$NR—, or —NRSO$_2$—; and each occurrence of $R^Y$ is independently R', halogen, NO$_2$, or CN, provided that:

g) when $R^1$ and $R^2$, taken together, are unsubstituted phenyl, then:
  i) when $X_1$ is CO, and $X_2$ is CH$_2$, then $R^3$ is not methyl, unsubstituted phenyl, substituted furyl, 2-Cl-phenyl, 3,5-dimethyl-2-benzofuranyl, 3,7-dimethyl-2-benzofuranyl, or 4-OMe-phenyl;
  ii) when $X_1$ is CO, and $X_2$ is NH, then $R^3$ is not methyl, C(O)CH$_3$; C(O)O(C$_{1-3}$alkyl), C(O)C(O)OH, C(O)C(O)O(C$_{1-3}$alkyl), unsubstituted phenyl, cyclohexyl, benzyl, substituted benzofuranyl, 2,4-dichloro-phenyl, 4-Cl-phenyl, or 4-Me-phenyl;
  iii) when $X_1$ is CO and $X_2$ is NMe, then $R^3$ not methyl;
  iv) when $X_1$ is CO and $X_2$ is O, then $R^3$ is not methyl;

i) when $X_1$ is CO, and $X_2$ is NH, then:
  i) when $R^1$ and $R^2$, taken together, are 6,7-dimethylphenyl, then $R^3$ is not n-hexyl, n-butyl, n-propyl, —CH$_2$CH=CH$_2$, —CH=N—CH$_2$CH=CH$_2$, C(=O)N(R)$_2$, —C(=O)OR wherein R is H or C$_{1-3}$ alkyl;
  ii) when $R^1$ and $R^2$, taken together, are 6-NHAc-7-Me-phenyl, then $R^3$ is not —C(=O)CH$_3$;
  iii) when $R^1$ and $R^2$, taken together, are 6,7-dimethoxyphenyl, then $R^3$ is not C(O)C(O)OH or C(O)C(O)O(C$_{1-3}$alkyl);

j) when $X_1$ is CO and $X_2$ is O, then:
  i) when $R^1$ and $R^2$, taken together, are 6,7-dichlorophenyl, then $R^3$ is not methyl or —CH$_2$CH=CH$_2$;
  ii) when $R^1$ and $R^2$, taken together, are 6-NO$_2$-7-F-phenyl, then $R^3$ is not methyl.

2. The compound of claim 1, wherein n is 0-4, and each occurrence of Q-$R^x$, when present, is independently halogen, CN, NO$_2$, or an optionally substituted group selected from C$_{1-4}$alkyl, a 5-6 membered monocyclic or an 8-10 membered bicyclic aryl group having 0-5 heteroatoms independently selected from nitrogen, oxygen, or sulfur; a 3-7-membered saturated or partially unsaturated monocyclic ring having 0-3 heteroatoms independently selected from nitrogen, oxygen, or sulfur; or an 8-10-membered saturated or partially unsaturated bicyclic ring system having 0-5 heteroatoms independently selected from nitrogen, oxygen, or sulfur; (C$_{1-6}$alkyl)-(5-6 membered aryl group); or (C$_{1-6}$alkyl)-(8-10 membered aryl group); —NRR', —CH$_2$NRR', —OR', —CH$_2$OR', —SR', —CH$_2$SR', —C(O)OR', —NRCOR', —CONRR', or —S(O)$_2$NRR'.

3. The compound of claim 2, wherein each occurrence of Q-$R^x$, when present, is independently halogen, CN, NO$_2$, or an optionally substituted group selected from C$_{1-4}$alkyl, —NRR', —CH$_2$NRR', —OR', —CH$_2$OR', —SR', —CH$_2$SR', —C(O)OR', —NRCOR', or —CONRR'.

4. The compound of claim 2 wherein n is 0.

5. The compound of claim 2 wherein n is 1.

6. The compound of claim 1, wherein n is 0, 1, or 2, wherein each occurrence of Q-$R^x$, when present, is Cl, Br, F, CF$_3$, methyl, ethyl, propyl, butyl, CN, —COOH, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —OCH$_2$CH$_2$CH$_3$, —OCH$_2$CH$_2$CH$_2$CH$_3$, —CH$_2$OH, —NHCOCH$_3$, —SO$_2$NH$_2$, —NHCO(pyridyl), —NHCONH$_2$, —NH$_2$, —NHCOCH$_2$N(CH$_3$)$_2$, —NHCOCH$_2$NH$_2$, or an optionally substituted group selected from piperidinyl, piperazinyl, morpholino, phenyl, phenyloxy, benzyl, benzyloxy, pyridyl, pyrimidinyl, pyridazinyl, thienyl, furanyl, thiazolyl, oxazolyl, thiadiazolyl, oxadiazolyl, pyrazolyl, or pyrrolyl.

7. The compound of claim 6 wherein each occurrence of Q-$R^x$, when present, is Cl, Br, F, CF$_3$, methyl, ethyl, propyl, butyl, CN, —COOH, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —OCH$_2$CH$_2$CH$_3$, —OCH$_2$CH$_2$CH$_2$CH$_3$, —CH$_2$OH, —NHCOCH$_3$, —SO$_2$NH$_2$, —NHCO(pyridyl), —NHCONH$_2$, —NH$_2$, —NHCOCH$_2$N(CH$_3$)$_2$, or —NHCOCH$_2$NH$_2$.

8. The compound of claim 6 wherein each occurrence of Q-$R^x$, when present, is an optionally substituted group selected from piperidinyl, piperazinyl, morpholino, phenyl, phenyloxy, benzyl, benzyloxy, pyridyl, pyrimidinyl, pyridazinyl, thienyl, furanyl, thiazolyl, oxazolyl, thiadiazolyl, oxadiazolyl, pyrazolyl, or pyrrolyl.

9. The compound of claim 1, wherein $X^1$ is C=O or SO$_2$.

10. The compound of claim 1, wherein $X^1$ is C=O and compounds have the structure:

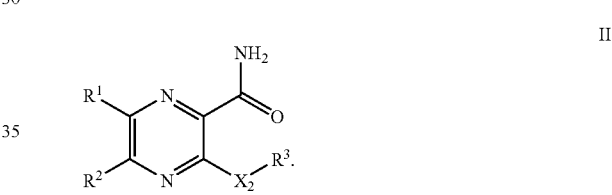

II

11. The compound of claim 10, wherein $X_2$ is NR, S, O, or C(R)$_2$.

12. The compound of claim 11, wherein $X_2$ is NR or C(R)$_2$.

13. The compound of claim 9, wherein $X_2$ is NR and compounds have the structure:

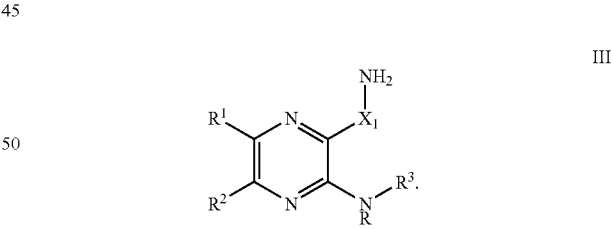

III

14. The compound of claim 13, wherein $X_1$ is C=O and $X_2$ is NR and compounds have the structure:

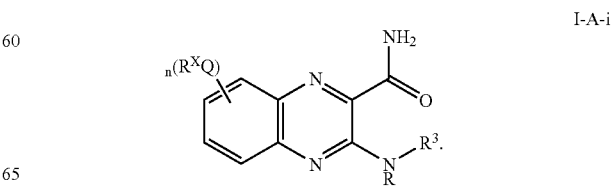

I-A-i

15. The compound of claim 1 or claim 14, wherein $R^3$ is a 5-6 membered monocyclic or an 8-10 membered bicyclic aryl group having 0-5 heteroatoms independently selected from nitrogen, oxygen, or sulfur; a 3-8-membered saturated or partially unsaturated monocyclic ring having 0-3 heteroatoms independently selected from nitrogen, oxygen, or sulfur; or an 8-10-membered saturated or partially unsaturated bicyclic ring system having 0-5 heteroatoms independently selected from nitrogen, oxygen, or sulfur.

16. The compound of claim 1 or claim 14, wherein $R^3$ is an optionally substituted $C_{1-6}$ aliphatic group, wherein the $C_{1-6}$ aliphatic group is optionally substituted with a 5-6 membered monocyclic or an 8-10 membered bicyclic aryl group having 0-5 heteroatoms independently selected from nitrogen, oxygen, or sulfur; a 3-8-membered saturated or partially unsaturated monocyclic ring having 0-3 heteroatoms independently selected from nitrogen, oxygen, or sulfur; or an 8-10-membered saturated or partially unsaturated bicyclic ring system having 0-5 heteroatoms independently selected from nitrogen, oxygen, or sulfur.

17. The compound of claim 15, wherein the 5-6 membered monocyclic or 8-10 membered bicyclic aryl group having 0-5 heteroatoms independently selected from nitrogen, oxygen, or sulfur; the 3-8-membered saturated or partially unsaturated monocyclic ring having 0-3 heteroatoms independently selected from nitrogen, oxygen, or sulfur; or the 8-10-membered saturated or partially unsaturated bicyclic ring system having 0-5 heteroatoms independently selected from nitrogen, oxygen, or sulfur is selected from one of the following groups:

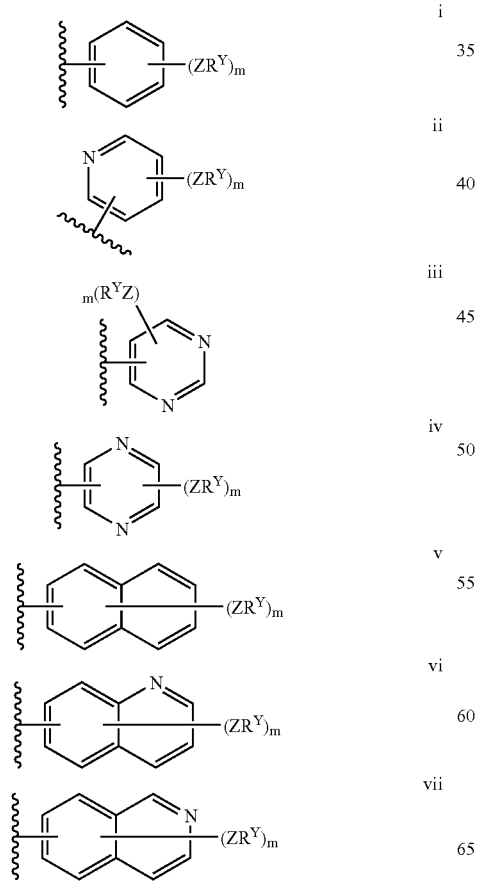

-continued

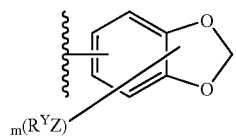

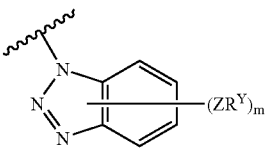

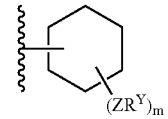

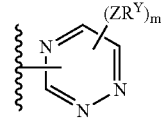

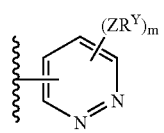

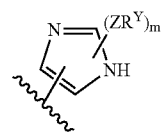

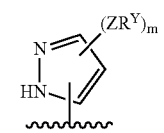

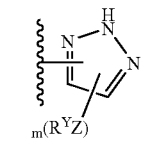

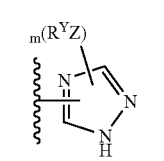

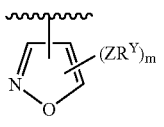

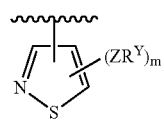

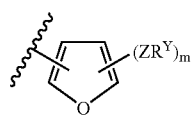 xx
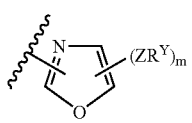 xxi
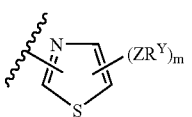 xxii
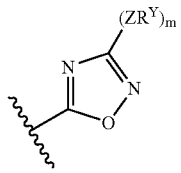 xxiii
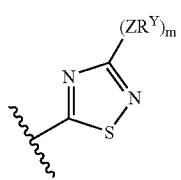 xxiv
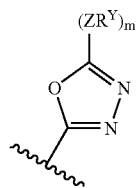 xxv
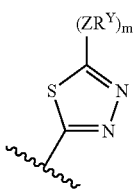 xxvi
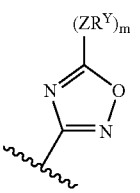 xxvii
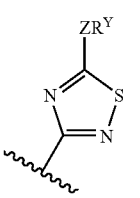 xxviii
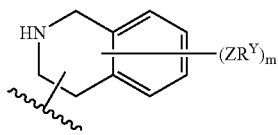 xxx
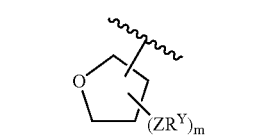 xxxi
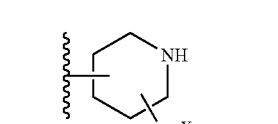 xxxii
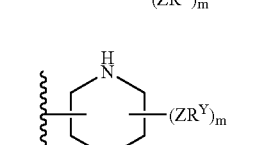 xxxiii
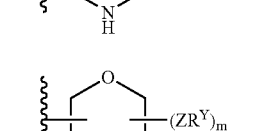 xxxiv
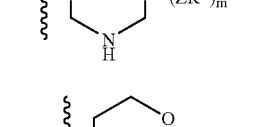 xxxv
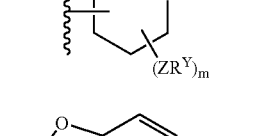 xxxvi
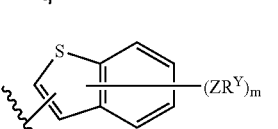 xxxvii
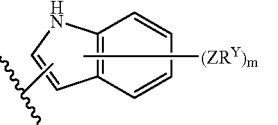 xxxviii
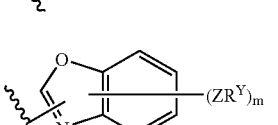 xxxviii
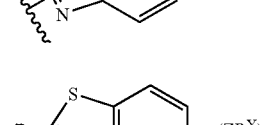 xxxix
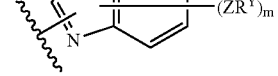 xL -continued

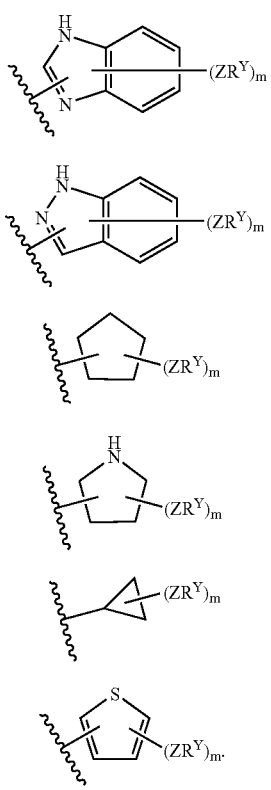

18. The compound of claim 17, wherein $R^3$ is an optionally substituted group selected from i, ii, xxxix, xL, xLi, or xLii.

19. The compound of claim 17, wherein $R^3$ is an optionally substituted phenyl group (i).

20. The compound of claim 1 or claim 14, wherein Z is a bond or is an optionally substituted $C_{1-6}$ alkylidene chain wherein one or two non-adjacent methylene units are optionally and independently replaced by —O—, —NR—, —S—, —$SO_2$—, or —C(O)O—, —CO—, and $R^Y$ is R' or halogen.

21. The compound of claim 1 or claim 14, wherein each occurrence of $ZR^Y$, when present, is independently —$C_{1-3}$ alkyl, —O($C_{1-3}$alkyl), —OH, —S($C_{1-3}$alkyl), —SH, $CF_3$, —$OCF_3$, —$SCF_3$, —F, —Cl, —Br, —CN, —COOR', —COR', —O($CH_2$)$_2$N(R)(R'), —$OCH_2$N(R)(R'), —CON(R)(R'), —NRCOR', —($CH_2$)$_2$OR', —$CH_2$OR', —N(R)(R'), —($CH_2$)$_2$N(R)(R'), —$CH_2$N(R)(R'), —$SO_2$N(R)(R'), —$NRSO_2$R', or an optionally substituted group selected from pyrrolidinyl, morpholino, piperazinyl, piperidinyl, phenyl, phenoxy, benzyl, benzyloxy, triazolyl, pyrazolyl, or pyridyl.

22. The compound of claim 1 or claim 14, wherein any substitutable nitrogen atom in an $R^3$ group is optionally substituted with Z-$R^Y$; wherein Z is a bond or $C_1$-$C_6$ alkylidene chain wherein 0 methylene units are replaced; and $R^Y$ is a 5-6 membered monocyclic or an 8-10 membered bicyclic aryl group having 0-5 heteroatoms independently selected from nitrogen, oxygen, or sulfur or wherein Z-$R^Y$ is —NRR', —$CH_2$NRR', —$CH_2$OR', —$CH_2$SR', —($CH_2$)$_2$NRR', —($CH_2$)$_2$OR', —($CH_2$)$_2$SR', —COR', —CONRR', —$SO_2$R', or —S(O)$_2$NRR'.

23. The compound of claim 1, wherein any substitutable nitrogen atom is optionally substituted with Me, $CF_3$, ethyl, propyl, butyl, pentyl, CO($C_1$-$C_4$alkyl), —$CONH_2$, —COO($C_1$-$C_4$alkyl), —$CH_2$OH, —$SO_2$($C_1$-$C_4$alikyl), —$SO_2NH_2$, $SO_2N(CH_3)_2$, or optionally substituted phenyl or benzyl.

24. A compound selected from:

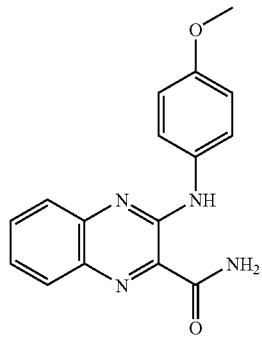

I-2

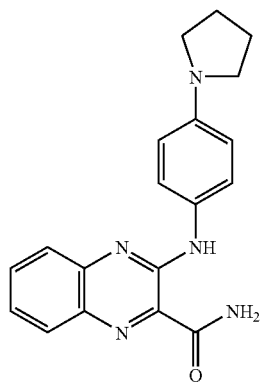

I-3

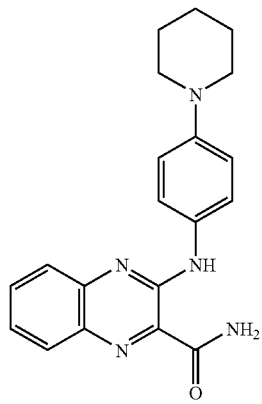

I-4

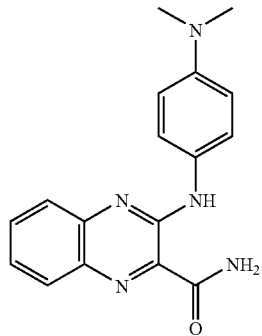

I-5

-continued
I-6
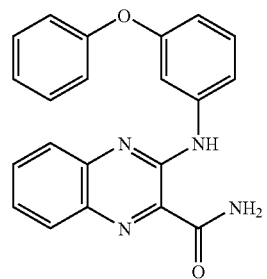
I-7
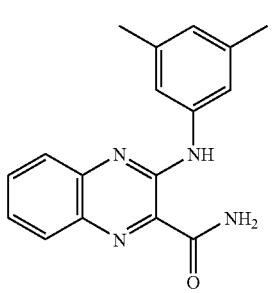
I-8
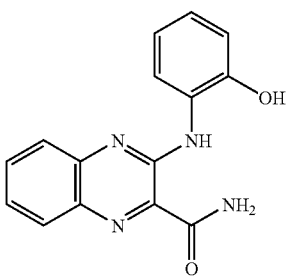
I-9
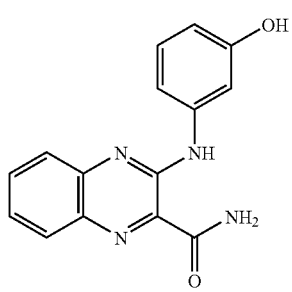
I-10
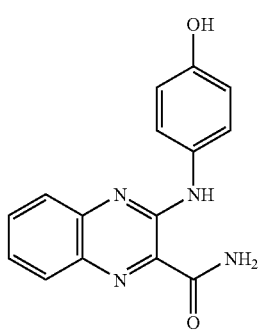
-continued
I-11
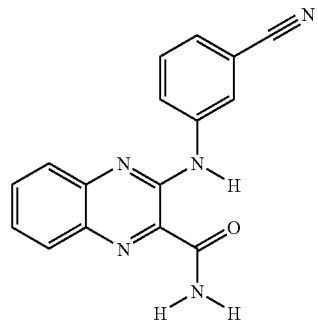
I-12
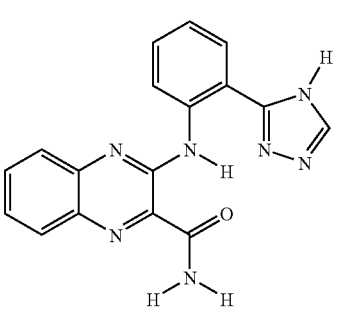
I-13
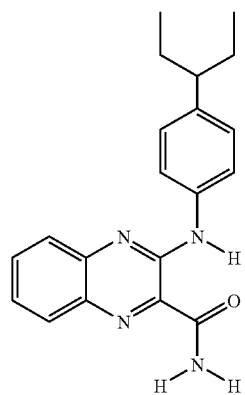
I-14
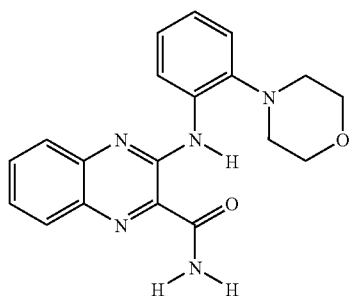

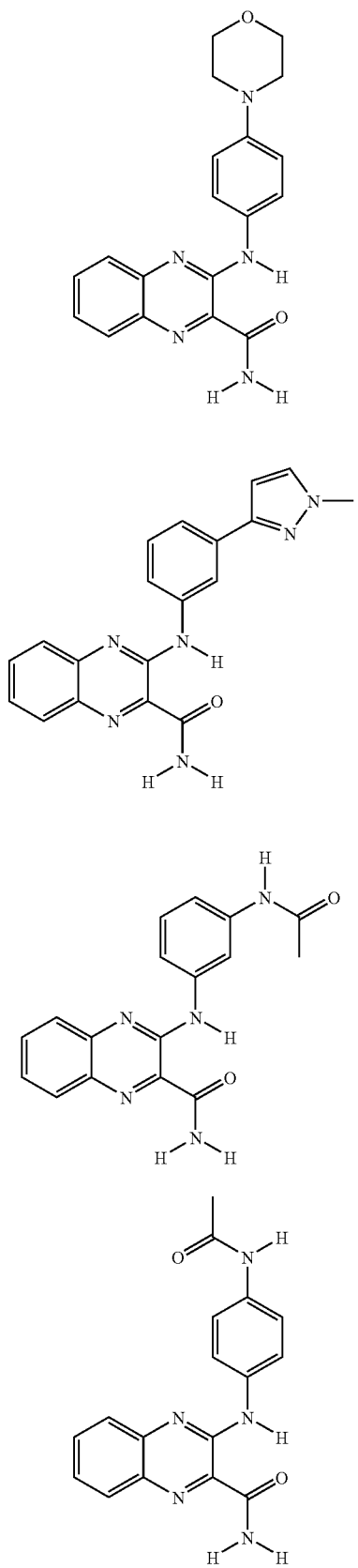
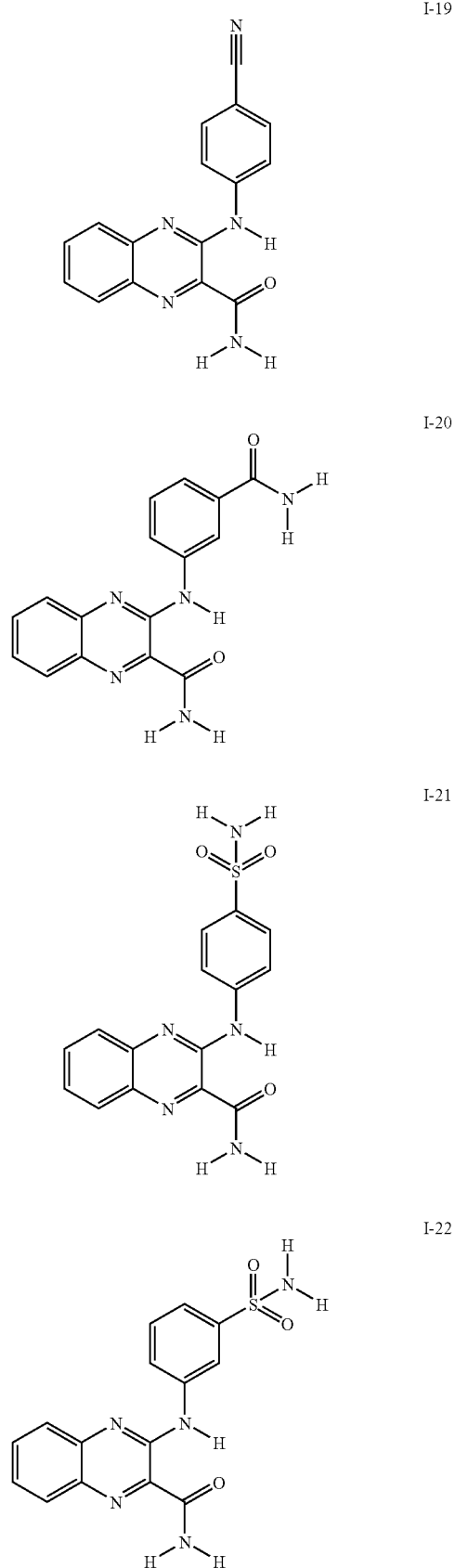

-continued
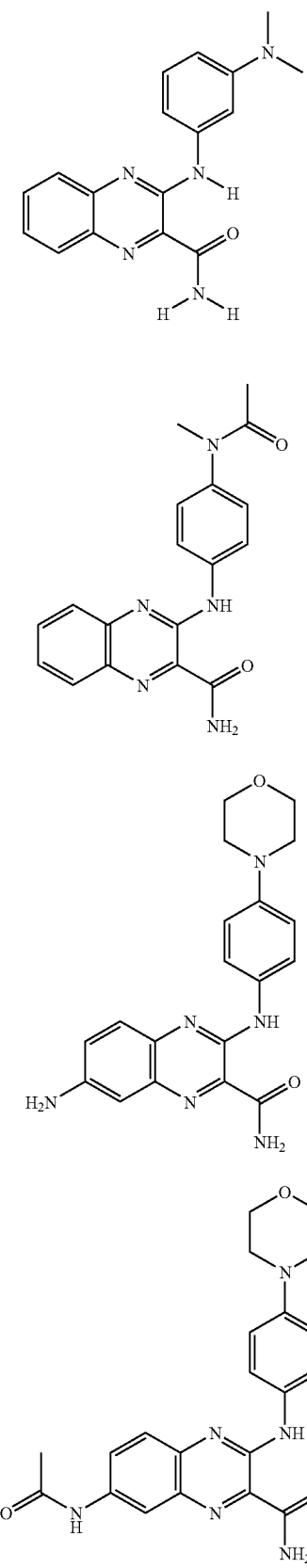
I-23
I-24
I-25
I-26
-continued
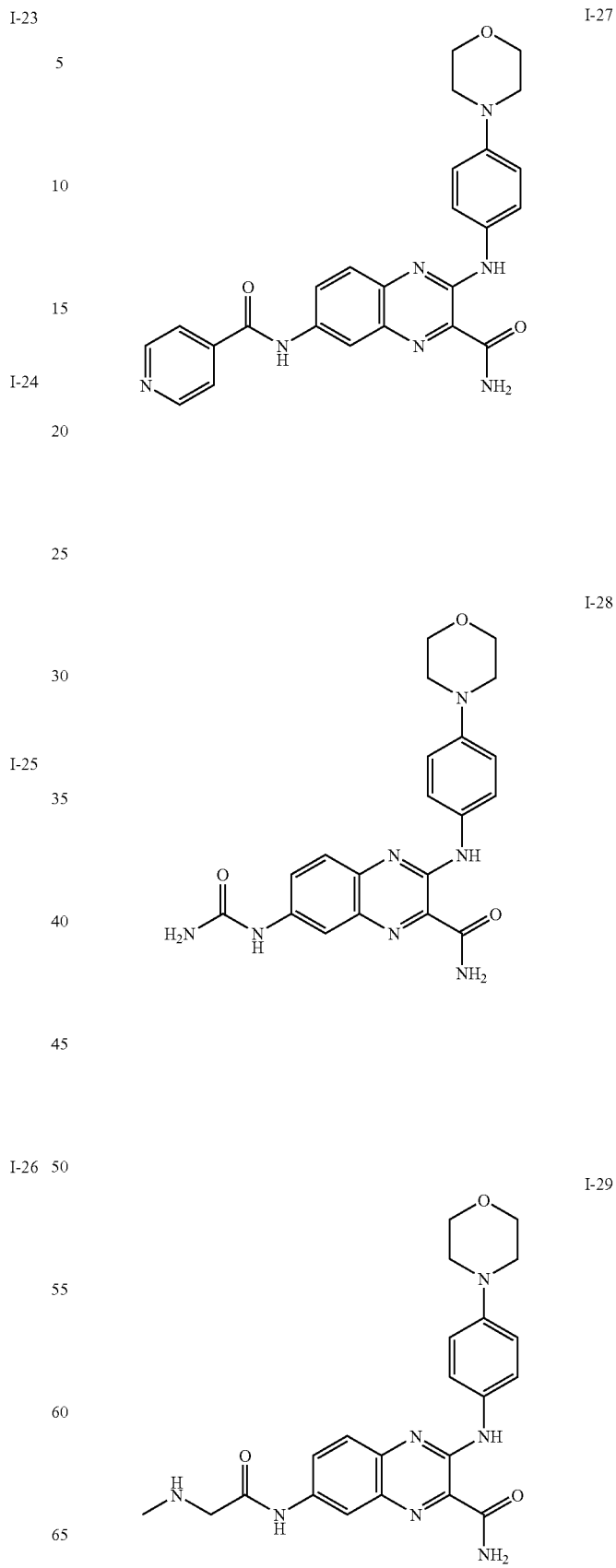
I-27
I-28
I-29

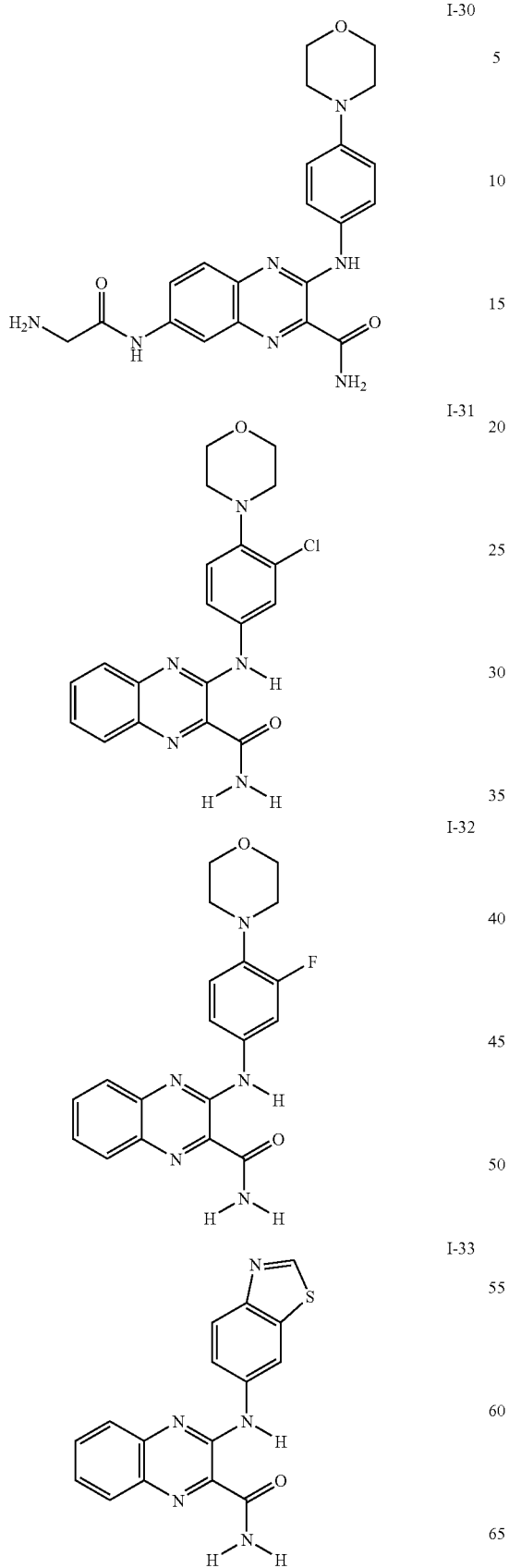
I-30
I-31
I-32
I-33
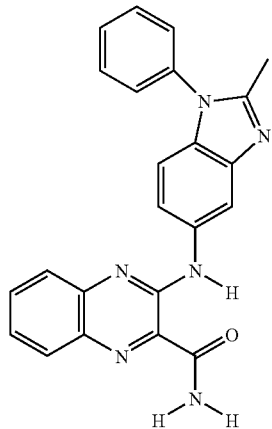
I-34
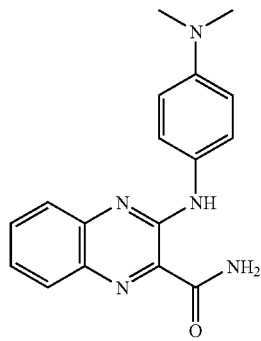
I-35
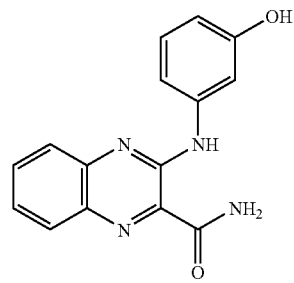
I-36
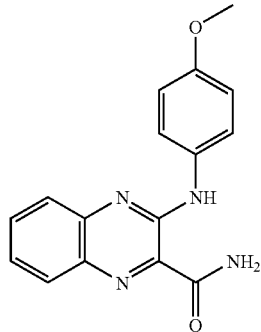
I-37

-continued
I-38 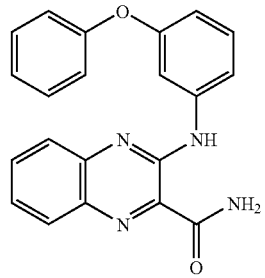
I-39 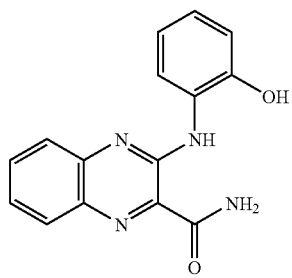
I-40 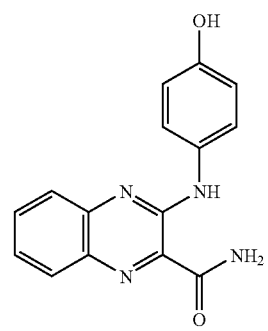
-continued
I-41 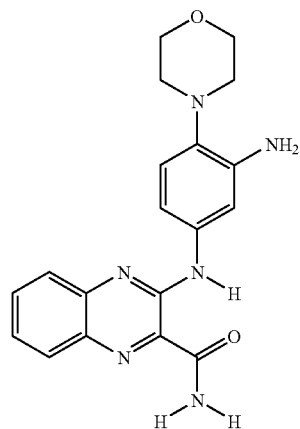
I-43 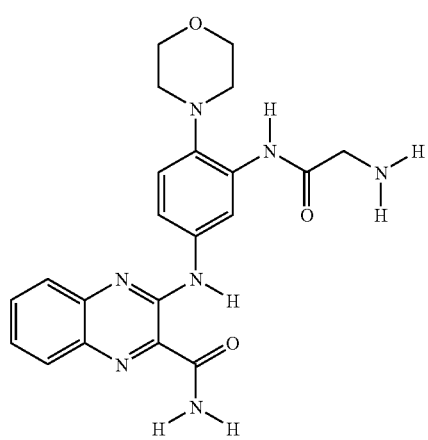
I-44 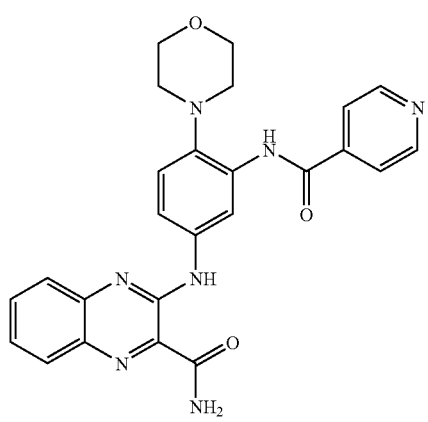

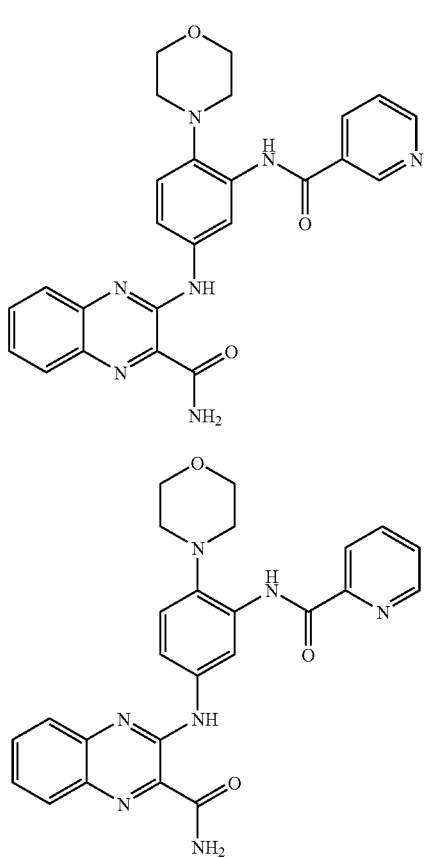

I-45

I-46

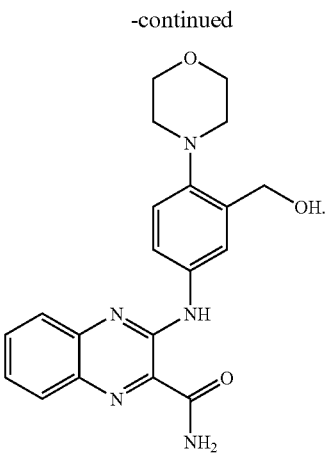

I-47

25. A pharmaceutically acceptable composition comprising a compound of claim 1, and a pharmaceutically acceptable carrier, adjuvant, or vehicle.

26. The compound of claim 6 or 14, wherein n is 0.

27. The compound of claim 6 or 14, wherein n is 1.

28. The compound of claim 14, wherein m is 1, and $ZR^Y$ is independently —O($C_{1-3}$alkyl), —OH, —S($C_{1-3}$alkyl), —SH, $CF_3$, —$OCF_3$, —$SCF_3$, —F, —Br, —CN, —COOR', —COR', —O($CH_2$)$_2$N(R)(R'), —$OCH_2$N(R)(R'), —CON(R)(R'), —NRCOR—, —($CH_2$)$_2$OR', —$CH_2$OR', —N(R)(R'), —($CH_2$)$_2$N(R)(R'), —$CH_2$N(R)(R'), —$SO_2$N(R)(R'), —$NRSO_2$R', or an optionally substituted group selected from pyrrolidinyl, morpholino, piperazinyl, piperidinyl, phenyl, phenoxy, benzyl, benzyloxy, triazolyl, pyrazolyl, or pyridyl.

* * * * *